United States Patent
Klein et al.

(10) Patent No.: US 10,662,438 B2
(45) Date of Patent: *May 26, 2020

(54) P0 GENE SILENCING CONSTRUCTS AND USE

(71) Applicant: SESVanderHave NV, Tienen (BE)

(72) Inventors: Elodie Klein, Strasbourg (FR); Véronique Graff, Strasbourg (FR); David Gilmer, Strasbourg (FR); Véronique Brault, Colmar (FR); Guy Weyens, Beersel (BE); Marc Lefebvre, Jodoigne Souveraine (BE)

(73) Assignee: SESVANDERHAVE NV, Tienen (BE)

( * ) Notice: Subject to any disclaimer, the term of this patent is extended or adjusted under 35 U.S.C. 154(b) by 151 days.

This patent is subject to a terminal disclaimer.

(21) Appl. No.: 15/908,729

(22) Filed: Feb. 28, 2018

(65) Prior Publication Data

US 2018/0265888 A1 Sep. 20, 2018

Related U.S. Application Data

(63) Continuation of application No. 14/128,962, filed as application No. PCT/EP2012/061436 on Jun. 15, 2012, now Pat. No. 9,932,603.

(30) Foreign Application Priority Data

Jun. 23, 2011 (EP) ..................................... 11171196

(51) Int. Cl.
*C12N 15/82* (2006.01)
*C12N 15/113* (2010.01)
*A01H 5/06* (2018.01)

(52) U.S. Cl.
CPC ............ *C12N 15/8283* (2013.01); *A01H 5/06* (2013.01); *C12N 15/113* (2013.01); *C12N 15/1131* (2013.01); *C12N 15/8218* (2013.01)

(58) Field of Classification Search
CPC .............. C12N 15/113; C12N 15/1131; C12N 15/8218; C12N 15/8283
See application file for complete search history.

(56) References Cited

U.S. PATENT DOCUMENTS

2006/0288445 A1* 12/2006 Lauber ................ C12N 15/8283
800/279

FOREIGN PATENT DOCUMENTS

| EP | 1169463 A1 | 1/2002 |
|---|---|---|
| WO | 91/13159 A2 | 9/1991 |
| WO | 00/44915 A1 | 8/2000 |
| WO | 2007/128755 | 11/2007 |
| WO | 2007/128755 A2 | 11/2007 |
| WO | 2009/141446 A1 | 11/2009 |
| WO | 2010/076212 A1 | 7/2010 |

OTHER PUBLICATIONS

Kozlowska-Makulska, Anna, et al. "P0 proteins of European beet-infecting poleroviruses display variable RNA silencing suppression activity." Journal of general virology 91.4 (2010): 1082-1091 (Year: 2010).*
Qu, Jing, Jian Ye, and Rongxiang Fang. "Artificial microRNA-mediated virus resistance in plants." Journal of virology 81.12 (2007): 6690-6699 (Year: 2007).*
Yan, Pu, et al. "Simple construction of chimeric hairpin RNA for virus resistance in plants." Journal of virological methods 166.1 (2010): 101-105 (Year: 2010).*
Eamens, Andrew, et al. "RNA silencing in plants: yesterday, today, and tomorrow." Plant physiology 147.2 (2008): 456-468 (Year: 2008).*
Guilley, Hubert, et al, Nucleotide sequence of beet mild yellowing virus RNA, Arch. Virol. 140 (6), 1109-1118 (1995) (Year: 1995).*
Nicholson, Beth L., Pui Kei K. Lee, and K. Andrew White. "Internal RNA replication elements are prevalent in Tonnbusviridae." Frontiers in microbiology 3 (2012): 279. (Year: 2012).*
Letter of Opposition issued in related European U.S. Pat. No. 2,723,873 B1, May 9, 2018.
3ortolamiol et al. "Viral suppression of RNA silencing by destabilisation of ARGONAUTE 1" Plant Signaling & Behaviour, 2008, vol. 3, Issue 9, 657-659.
Yi Chuan. et al. "Transgenic wheat expressing virus-derived hairpin RNA is resistant to Barley yellow dwarf virus." Yi chuan=Hereditas/Zhongguo Yi chuan xue hui bian ji 29.1 (2007): 97-102.
Collinge et al., "Engineering Pathogen Resistance in Crop Plants: Current Trends and Future Prospects", Annu. Rev. Phytopathol., 2010, 48, 269-291.
Dohm et al. "The genome of the recently domesticated crop plant sugar beet (*Beta vulgaris*)". Published in Nature. Jan. 23, 2014;505(7484):546-549.
Fahim et al., "Hairpin RNA derived from viral Nia gene confers immunity to wheat streak mosaic virus infection in transgenic wheat plants", Plant Biotechnology Journal, 2010, 8, 821-834.
Lennefors et al. "dsRNA-mediated resistance to Beet Necrotic Yellow Vein Virus infections in sugar beet (*Beta vulgaris* L. ssp. *vulgaris*)", Molecular Breeding, 2006, 18, 313-325.
Lennefors et al. "Efficient dsRNA-mediated transgenic resistance to Beet necrotic yellow vein virus in sugar beets is not affected by other soilborne and aphid-transmitted viruses", Transgenic Res., 2008, 17, 219-228.

(Continued)

Primary Examiner — Weihua Fan
(74) *Attorney, Agent, or Firm* — Merchant & Gould P.C.

(57) ABSTRACT

The present invention include a recombinant BMYV P0 viral nucleotide sequence, which when transcribed in a cell, is capable of forming a double stranded self-complementary RNA sequence. The invention is related to a method for conveying viral resistance or tolerance to one or more virus(es), in particular to beet mild yellowing virus (BMYV) and to beet necrotic yellow vein virus (BNYVV) or to BMYV alone in a plant, in particular in a sugar beet plant. Furthermore, the present invention relates to the virus-resistant or -tolerant plant obtained according to this method, as well as to seeds and progeny derived therefrom.

17 Claims, 13 Drawing Sheets

Figure 4A:
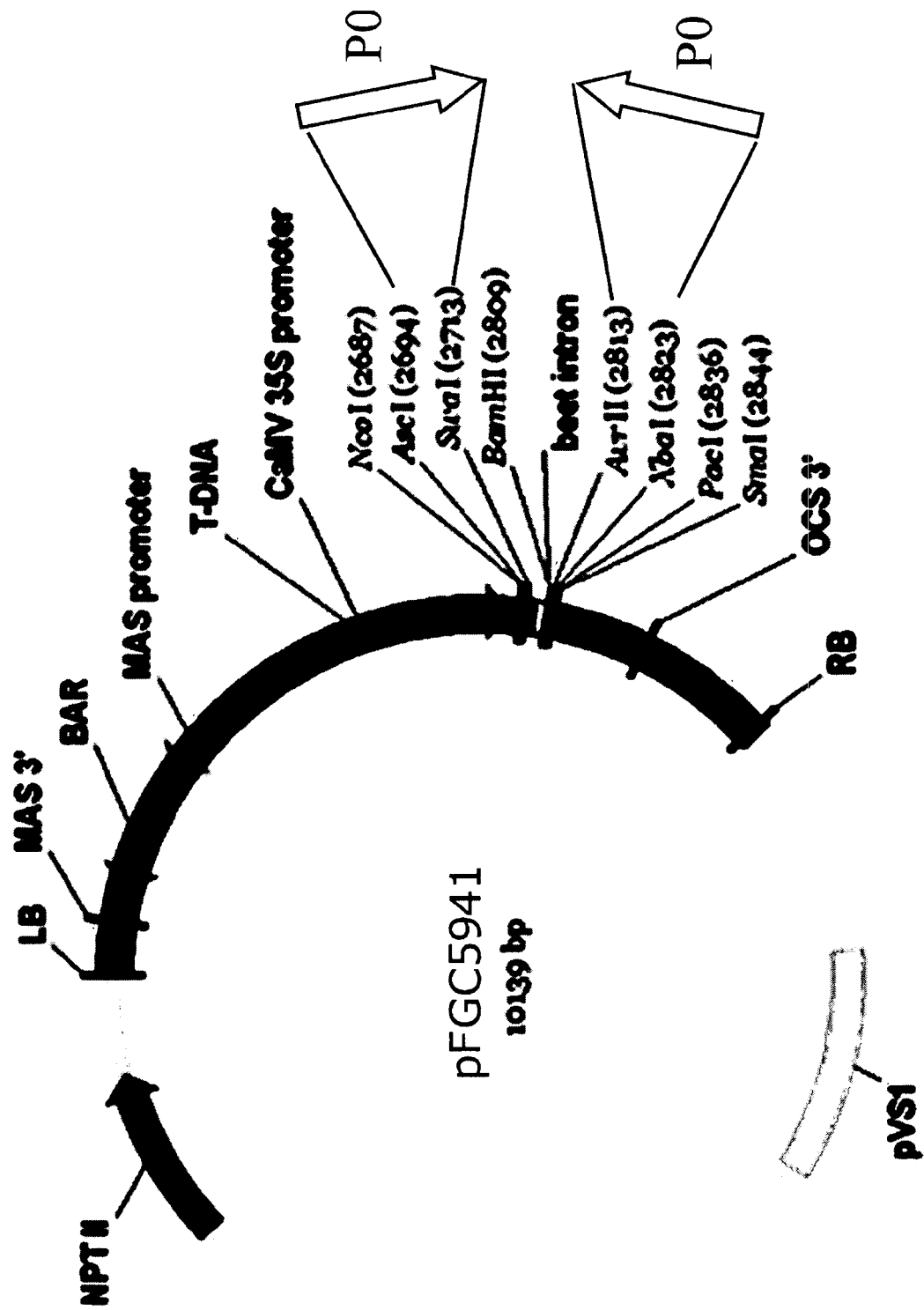

Specification includes a Sequence Listing.

(56) References Cited

OTHER PUBLICATIONS

Marcais, G. and Kingsford, C. "A fast, lock-free approach for efficient parallel counting of occurrences of kmers." Published in Bioinformatics. Mar. 15, 2011;27(6):764-770.
Missiou et al. "Generation of transgenic potato plants highly resistant to potato virus Y (PVY) through RNA silencing." Molecular Breeding, 2004, 14, 185-197.
Patil et al., "RNAi-mediated resistance to diverse isolates belonging to two virus species involved in Cassava brown streak disease", Molecular Plant Pathology, 2011, 12(1), 31-41.
Pazhouhandeh et al. "F-box-like domain in the polerovirus protein P0 is required for silencing suppressor function." PNAS, 2006, vol. 103, No. 6, 1994-1999.
Pfeffer et al. "P0 of Beet Western Yellows Virus is a suppressor of posttranscriptional gene silencing" Journal of Virology, 2002, vol. 76, No. 13, 6815-6824.
Praveen et al., "Silencing potential of viral derived RNAi constructs in Tomato leaf curl virus-AC4 gene suppression in tomato.", Transgenic Res., 2010, 19(1 ), 45-55.
Sadowy et al. "The ORF0 product of Potato leafroll virus is indispensable for virus accumulation." Journal of General Virology, 2001, 82, 1529-1532.
Schwind et al., "RNAi-mediated resistance to Potato spindle tuber viroid in transgenic tomato expressing a viroid hairpin RNA construct", Molecular Plant Pathology, 2009, vol. 10, No. 4, 459-469.
Sun et al., "Bacterially Expressed Double-Stranded RNAs against HotSpot Sequences of Tobacco Mosaic Virus or Potato Virus Y Genome Have Different Ability to Protect Tobacco from Viral Infection.", Appl. Biochem. Biotechnol., 2010, 162(7), 1901-1914.
Vanderschuren et al. "Transgenic cassava resistance to African cassava mosaic virus is enhanced by viral DNA-A bidirectional promoter-derived siRNAs", Plant Mo/. Biol., 2007, 64, 549-557.
Kalantidis, Kriton, et al. "Generation of 13k-Gene Sugar Beet Transformants and Evaluation of Their Resistance to BNYW Infection." Developments in Plant Genetics and Breeding 6 (2000): 189-194.
Zamore et al., "RNAi: Double-Stranded RNA Directs the ATP-dependent Cleavage of mRNA at 21 to 23 Nucleotide Intervals", Cell, 2000, vol. 101, 25-33.
Zhang et al., "RNA Interference-Based Transgenic Maize Resistant to Maize Dwarf Mosaic Virus", J. Plant Biol., 2010, 53, 297-305.
Carole L. Thomas et al., "Size constraints for targeting post-transcriptional gene silencing and for RNA-directed methylation in Nicotiana benthamiana using a potato virus X vector", The Plant Journal.vol. 25, Issue 4, Feb. 2001, pp. 417-425.
Csorba, Tibor, et al. "Polerovirus protein P0 prevents the assembly of small RNA-containing RISC complexes and leads to degradation of ARGONAUTE1 "The Plant Journal 62.3 (2010): 463-472.
David Abbott et al., "A Single Copy of a Virus-Derived Transgene encoding Hairpin RNA Gives Immunity to Barley Yellow Dwarf Virus", Australian Barley Technical Symposium, 2001, available on line at http:f/www.regional.org.au/au/iibts/2001/m4/abbott.htm.
David L. Beck et al., "Disruption of virus movement confers broad-spectrum resistance against systemic infection by plant viruses with a triple gene block", Proceedings of the National Academy of Sciences of the United States of America, vol. 91, No. 22, Oct. 25, 1994, pp. 10310-10314.
Andrew Eamens et al. "RNA silencing in plants: yesterday, today, and tomorrow" Plant physiology 147.2 (2008): 156-468.
Elisa Di Nicola-Negri et al., "Hairpin RNA-mediated silencing of Plum pox virus P1 and HC-Pro genes for efficient iind predictable resistance to the virus", Transgenic Research, vol. 14, Issue 6, Dec. 2005, pp. 989-994.
Gert E. de Vries et al., "Generation of 13k-Gene Sugar Beet Transformants and Evaluation of their Resistance to BNYVV Infection", Phytosfere'99—Highlights in European Plant Biotechnology, Nov. 7, 2000, pp. 189-194.
Gurney, Hubert, et al, Nucleotide sequence of beet mild yellowing virus RNA, Arch. Virol. 140 (6), 1109-1118 (1995).
International Search Report from International Application No. PCT/EP2012/061436 dated Sep. 21, 2012.
Kovalev, Nikolay, Judit Pogany, and Peter D. Nagy. "Template role of double-stranded RNA in tombusvirus replication." Journal of virology 88.1 0 (2014): 5638-5651.
Kozlowska-Makulska et al., "P0 proteins of European beet-infecting poleroviruses display variable RNA silencing suppression activity", Journal of General Virology, vol. 91, 2010, pp. 1082-1091.
Maghsoud Pazhouhandeh et al., "F-box-like domain in the polerovirus protein P0 is required for silencing suppressor function", Proceedings of the National Academy of Sciences of the United States, vol. 103, No. 6, Feb. 7, 2006, pp. 1994-1999.
Nicholson, Beth L., Pui Kei K. Lee, and K. Andrew White. "Internal RNA replication elements are prevalent in Tombusviridae." Frontiers in microbiology 3 (2012): 279.
Pavli, Ourania, "Molecular Characterization of Beet Necrotic Yellow Vein Virus in Greece and Transgenic Approaches towards Enhancing Rhizomania Disease Resistance", Thesis for the degree of doctor at Wageningen University, NL, 2010, pp. 1-166.
Qu, Jing, Jian Ye, and Rongxiang Fang. "Artificial microRNA-mediated virus resistance in plants." Journal of virology, vol. 81, No. 12 (Jun. 2007): 6690-6699.
Sasaya, Takahide, et al. "Transgenic strategies to confer resistance against viruses in rice plants." Frontiers in microbiology 4 (2014) : 409.
Sequence Listing from European Patent Publication No. 2,723,873 for the Plum Pox Virus Strain M.
Simon-Mateo et al., "Antiviral strategies in plants based on RNA silencing", Biochimica et Biophysica Acta, vol. 1809, 2011, pp. 722- 731.
Tenllado et al., "RNA interference as a new biotechnological tool for the control of virus diseases in plants", Virus Research, vol. 102, 2004, pp. 85-96.
Yan et al., "Simple construction of chimeric hairpin RNA for virus resistance in plants", Journal of Virological Methods, vol. 166, 2010, pp. 101-105.
Yan et al., "Transgenic Wheat Expressing Virus-Derived Hairpin RNA is Resistant to Barley Yellow Dwarf Virus", Yi Chuan, vol. 29, No. 1, Jan. 2007, pp. 97-102, abstract only.
Decision of the Opposition Division from corresponding European Application No. 12728499.0, dated Jul. 30, 2019.

* cited by examiner

FIG. 1A

| P0 sense | CHSA Intron (1352bp) | P0 antisense |
|---|---|---|

FIG. 1B

P0 sense

CAAAGAAACCAGGCGAGGATCTAGCAGTCTATGCAATTTCAGCTTAAAACAAACA
GTTTCACTTGTTCGTTGAACCGACCGACTAACGCTACGACGAGCGAGTTTAAACAC
CGCGTATTTTCTTACGAATCATTTACCGCTCGTAACTTTTGAGAATGAAAACTGTA
TTCGTTCTCTTCTCGCTCGGGAAACGCCAGTCTCTTACGACTCGAGTAAGCAGCTCA
AGCTTTATTTACGCTCCCGGAAACGCCAGTCTCTTACGACTGCCAGGTTCTCA
ATTACTGCGGAGCGCGTGTTACCGCAACATTGACTTACGAGTGCCCC
CAGAAAAGACGTTTAAAGATTTTACCTTGCCCGAAATTCAGGCAGATCTGGG
GGAGAGGCTACAACGCCCCAGAGAAATTTTCTCTCGCGGTGAAGCAGAGTTTAA
AAAGTTCCTTTCAGTAGGTGTGACCATATATTATTATGGTCTTACGCGATATGGGCACTC
AAAATCGATATAGAATGGACCATATATTATTATGGTCTTACGCGATATGGGCACTC
TCTTGCACCGTCTGGTACTTGTTGAAGAACTATACCATAGAAATACTTATGCTGA
GCTCGCTTTTTGCGTCACCACCTTTTGTGAAGCTCGTGGTATTGGATTTTGCCT
AGGAATTTAAATGTGTAAGAATTTCTTATGTTACATTATTACATTTCATTCACGTTTT

CHSA intron

ATCTTAATTGGCTCTCATTTTTGTGGTGGGTCTGATTGACAATTATTTCTGTTTTT
TTTTGTCACACTCTTTTGGGTGGGGTGGCCGACGAATAGTAACTGTTCCGTTTCA
AAAGAGGGAGGACTTTGTATATCCATAGTAACTATTCGTTCCGTTTCA
ATTTATGTGACAATATTTCCTTTTAGTCGTTCCAAAAGAAAATGTCAGCAT
TATAAACAATTTTAATTTGAAATTACAATTTGCCATTAATAAATGATTTAC
AACCACAAAAGTATCTATGAGCCTGTTTGGGTGGCTTAAGCAGCTTATT
TTAAGTGGCTTATAAAAGTCAAAAAGTGACANTTTTGAGAAGTTAGAAAATCC
TAACTTCTCAAAAATAGCTTTAAGCACTTATGACTTATAAGTCAAAAAT
TTTAAGTTACCAAACATATATTAATTGGTTTATAAGCTTATAAGCCACTTT
AAGCTCACCCAAACGGGTTCTATGTCTCCACTTTAGACTACAAATTTAAAGT
CTTCATTTATTCTTAATCTCCGTGGCAGTAAACTATTAATCCAAATCAACATAAGTGA
AACGGAGGAATAAGAATGGAGTCATAAACTAATCAACATAAACAGATTTTCGAA
GTTAATTGTTTTTTAGTTGATTTGGGTACATTGAGTTAAAACAGATTTTCGAA
GGTTAAACACAGACAGATGTTTCCCAGCAGCATAGCAGAATTCCAAGATT
TCTGTCGAAAATTCGTGTGTTTCTAGCTAGTACTGATCTTATCTTTAACCTT
AGTAATTTTTGTCTTTCTCCTATTTCTCATCCATCTAATAATGAATTATGAG
CAAGTTCCTTAAGTAGCACACGTAGAATTGTTTTTATTGACTATTGACTAA
TCCAATCTTACCATTCCTAACTAGTAAAATACAACATGTTAATTGATAC
ATTGCTTAACACTGAGTTAGAAATTTTGAAATTAGTTGTCAAATGCTTT
GAAATTTAAAAATCTTTAATCCTTATTTTTTTAAAATGTTTTCTCACTCC
AAAGAAGAAACTGACATGTACATGAAGCTCAAAGATCAAAGATCTTACTAACT
TGTGGAACTAAATGTACATGAAGCTCAAAGATCAAAGATCTTACTAACT
CTTAATTCTTCTTTATTATTGAGGGTTTTCATGCTATGCATTCAATT
GAGTACTTTAAAGCACCTATAAACCACTTTCGTGACATGCTCTTGGAGTTTATG
TTTAGTGTTTCTTCACATCTTTGTCAGGTATTTGGATCCTAG

P0 antisense

GCAAAAATCCATACCACGAGCTTCACCAAAAGGTGCTGAACGCAAAAGCG
AGCTCAGCATAAGTATTTCTATGCTATAGTTCTTCAACAAGTACCAGACGGT
GCAAGAGAGTGCCCATATCGCGTAAGACCATAATAATGTCCATTCTAAT
ATCGATTTAGGACTCTCCCGTAGCTTCTCCGCTTTCAGCACACCATACTG
AAAGGAACTTTTAATCTTTAATTCCTTCACGCCGAGAAAATTTCTCTGCGCG
TTGTAGCCTCTCCCCAGATCTCTGCCTGAATTTCGGGCAAGTAAAATCTT
TTAACGTTCTTTTCTGGGGGCACTCGTAAGTCAATGTTGCGAGTGCTGGTA
ACACGGCTCCGACTAATTGTAGAACCTGGCCAGTCGTAAAGACTGGCGTTT
CCCGGAGCGTAAATAAAGCTCCCGGGCTGCGAGCTGCTTACTGCAGCAA
AGGCAGAGCAGCGAGAAGAGAACGAATACAGTTTCATTCTCAAAGTTACG
AGCGGTAAATGATTCGTAAGAAAATACGGCGTGTTTAAACTCGCTCTGTAG
CTGTTAGCGCTCGGTTCAACGAACAGATCCTGCTGGTTCTTTTG
TTGCATAGACTGCTAGATCCTCGCTGGTTCTTTG

Fig. 1

FIG. 2A

| P0 sense | Beet intron (91bp) | P0 antisense |

FIG. 2B

*CAAAAGAAACCAGGAGGATCTAGCAGTCT*ATGCAATTTCAGCTTAAAACAAACA
GTTTCACTTGTTCGTTGAACCGACCGCTAACAGCTACAGAGCGAGTTTAAACAC
CGCGTATTTCTTACGAATCATTTACCGCTCGTAACTTTTGAGAATGAAAACTGTA
TTCGTTCTCTCGCTGCTCTGCCTTGCTGTCAGTAAGCAGCTCGACCCGGG
AGCTTTATTACGCTCCCGGAAACGCCAGTCTTTACGACTGCCAGTTCTACA
ATTACTGCGGAGCCGTGTTACCAGCACTCGCAACATTGACTTACGAGTGCCCC
CAGAAAAGACGTTAAAGATTTACCTTGCCCGAAATTCAGGCAGAGATCTGGG
GGAGAGGCTACAACGCCGCAGAGAATTTTCTCGCGGTGAAGCAGAGTTTAA
AAAGTTCCTTTCAGTATGGTGTGCTGAAAGCGAGAGAAAGCTACGGGAGAGTCCT
AAAATCGATATTAGAATGGACCATATTATTGACCATATATGGTCTTACGCGATATGGCACTC
TCTTGCACCGTCTGGTACTTGTTGAACCACCTTTTGGTGAAGCTCGTGGTATGGATTTTG*CCT*
GCTCGCTTTTGCCTTCACCACCTTTTGGTGAAGCTCGTGGTATGGATTTTG*CCT*
*AGGAATTTAAATTAAATCCTGTTTATATGTACTGTTGTGAAATTT*
AGTCTCTTCTGCTGAATTTATTCTGTTTCGTTTCACTGTTATTCAGG*GGATC*
*CTAGG*CAAAAATCCATACCACGAGCTTCACCAAAAAGGTGGTGAACGCAAAA
AGCGAGCTCAGCAGAGAATGTATTCTATGCGTAAGTAGTCTTCAACAAGTACCAGA
CGGTGCAAGAGAGTGCCCATATCGCGTAAGACCATATAATATGGTCCATTC
TAATATCGATTTGAGACTCTCCCGTAGCTTCTCTCGCTTCAGCACACCAT
ACTGAAAGGAACTTTAAACTCTGCTTCACCGCGAGAGAATTTCTCTGC
GGCGTTGTAGCCCTCTTTTCTGCCCCCAGATCTCTGCCTGAATTTCGGGCAAGGTAAA
TCTTTTAACGTCTTTTCTGGGGACTCGTAATTGTAGAACCTGGCCAGTCGTAAAGACTGG
GGTAACACGGCTCCCGGAGCTCAGTAATTGTAGAACCTGGCCAGTCGTAAAGACTGG
CGTTTCCCGGAGCGTAAATAAGCTCCCGGGTCGAGCTGCTTACTGAGC
AGCAAAGGCAGAGCAGGGTAAATACGGAGAAGAGAATACAGTTTTCATTCTCAAAA
GTTACGAGCGGTAAATGATTCGTAAGAAATACGCGGTGTTTAAACTCGCT
CTGTAGCTGTTAGCGGTCGGTTCAACGAACAAGTGAAACTGTTGTTTTAAG
CTGAAATTGCATA*GACTGCTAGATCCTCGCTGGTTTCTTTTG*

Fig. 2

Sequence Range: 1 to 659

```
         10        20        30        40        50        60        70        80        90       100
CAAAAGAAACCAGCGAGGATCTAGCAGTCTATGCAATTTCAGCTTAAAAACAACAGTTTCACTTGTTCGTTGAACCGACCGCTAACAGCTACAGAGCGAG
        110       120       130       140       150       160       170       180       190       200
TTTTAAACACCGCGTATTTTCTTACGAATCATTACCGCTCGTAACTTTTGAGAATGAAAACTGTATTCGTCTCTTCGCTGCTCTGCCTTTGCTGCT
        210       220       230       240       250       260       270       280       290       300
CAGTAAGCAGCTGACCCCGGGAGCTTTATTTACGCTCCCGGGAAACGCCAGTCTTTACGACTGGCCAGGTTCTACAATTACTGCGAGCCGTGTTACCC
        310       320       330       340       350       360       370       380       390       400
AGCACTCGCAACATTGACTTACGAGTGCCCCCAGAAAAGACGTTAAAAGATTTTACCTTGCCCGAAATTCAGGCAGAGATCTGGGGAGAGGCTACAAC
        410       420       430       440       450       460       470       480       490       500
GCCGAGAGAAATTTCTCGCGGTGAAGCAGAGTTCCTTTCAGTATGGTGTGCTGAAAGCGAGAGAAAGCTACGGGAGAGTCCTAAAAT
        510       520       530       540       550       560       570       580       590       600
CGATATTAGAATGGACCATATTATGTCTTACGCGATATGGCACTCTCTTGCACCGTCTGGTACTTGTTGAAGAACTATACCATAGAAATACTTAT
        610       620       630       640       650
GCTGAGCTCGCTTTTGCGTTCACCACCTTTTTGGTGAAGCTCGTGTATGGATTTTTG
```

Fig. 3

Sequence Range: 1 to 720

```
          10         20         30         40         50         60         70         80         90        100
ATGCAATTTCAGCTTAAAACAAACAGTTTCACTTGTTCGTTGAACCGACCGCTAACAGTACAGAGCGAGTTTAAACACCGCGTATTTCTTACGAATC
 M  Q  F  Q  L  K  T  N  S  F  T  C  S  L  N  R  P  L  T  A  T  E  R  V  L  N  T  A  Y  F  L  T  N
         110        120        130        140        150        160        170        180        190        200
ATTTACCGCTCGTAACTTTGAGAATGAAAACTGTATTCGTTCTTCTCGCTCGTTGCTGCCTTTGTGCTGCTCAGTAAGCAGCTCGACCCGGGAGCTTAT
 I  T  R  S  L  L  A  A  L  P  L  L  L  S  K  Q  L  D  P  G  S  F  I
         210        220        230        240        250        260        270        280        290        300
HLPLVTFFENENCIRS
CACCTCCCGGGAAACGGCCAGTCTTACGACTGGCCAGTTCTACAATTACTGCGAGCCGTGTTACCAGCACTGCAACATTGACTTACGAGTGCCC
 H  L  P  L  V  T  F  F  E  N  E  N  C  I  R  S  L  L  A  R  F  Y  N  Y  C  G  A  V  L  P  S  T  R  N  I  D  L  R  V  P
         310        320        330        340        350        360        370        380        390        400
TTACGCTCCCGGGAAACGGCCAGTCTTACGACTGGCCAGTTCTACAATTACTGCGAGCCGTGTTACCAGCACTGCAACATTGACTTACGAGTGCCC
 Y  A  P  G  K  R  Q  S  L  R  L  A  R  F  Y  N  Y  C  G  A  V  L  P  S  T  R  N  I  D  L  R  V  P
         410        420        430        440        450        460        470        480        490        500
CCCAGAAAAGACGTTAAAAGATTTACCTTGCCCGAAATTCAGGAGACTGGGGAGGAGCTACAACGCCGCAGAGAATTTCTCTCGGGTGAAG
 P  R  K  D  V  K  R  F  Y  L  A  R  N  S  G  R  D  L  G  E  R  L  Q  R  R  R  E  I  F  S  R  G  E
         510        520        530        540        550        560        570        580        590        600
CAGAGTTTAAAAGTTCCTTCAGTATGGTGCTGAAAGCGAGAAAGCTACGGAGAGTCCTAAAATCGATATTAGAATGGACCATATTATGGT
 Q  S  L  K  V  P  S  V  M  V  L  K  A  R  K  A  T  E  S  P  K  I  D  I  R  M  D  H  I  M  V
AEFKKFLSVWCAESERKLRESPKIDIRMDHIMV
         610        620        630        640        650        660        670        680        690        700
CTTACGCGGATATGGGCACTCTCTTGCACCGTCTGGTACTTGTTGAAGAACTATACCATAGAAATACTTATGCTGAGCTCGCTTTTGCGTTCACCACCTT
 L  R  D  M  G  T  L  L  H  R  L  V  L  V  E  E  L  Y  H  R  N  T  Y  A  E  L  A  F  C  V  H  H  L
         710        720
TTTGGTGAAGCTCGTGCTGGTATGGATTTTTGGCGGTTGGCTAACTTCCCTGTAAACTTGGTTATTTGCTCTCACGAAATGTATTTTGAAAACTCTTTCATCC
 F  G  E  A  R  G  M  D  F  W  R  L  A  N  F  P  G  K  W  F  I  C  S  H  E  M  Y  F  E  N  S  F  I
AGAAAGAGCTACGTTTGTGA
 Q  K  E  L  R  L  *
```

Fig. 8

FIG. 9A

[Diagram: P15A4-P0 sense — Beet intron (91bp) — P15A4-P0 antisense]

FIG. 9B

P15A4-P0 sense

```
GGTGCTTGTGGTTAAAGTAGATTTATCTAATATTGTATTGTACATAGTTGCCGGTTGTGT
TGTTGTCAGTATGTTGTACTCACCGTTTTCAGCAACGATGTTAAGCGTCCAGCTATGC
GGGAGCAATTTTTAAGGGGAGCGGCTGTTATCATGCGCGAATTCGTTTGCTCAATTTG
GGAGTTGCGATATTCCAAAGCATGTAGCCGAGTCCATCACTAAGGTTGCCACCAAGA
GCACGATGTTGACATATGTGTAAAAGGGTGAGTGTTTGGTTTGGCGTGTGTGACTCTCA
CCGAAACTATTTTTATAATATTATTCTAGATTGTTTGGTTTGGCGGTGTTTTGTTCATGAT
ATGTTTAATGTCTATAGTTTGGTTTGGTATCATAGATAACAAAAGAAACCAGCAGGA
TCTAGCAGTCTATGCAATTTCAGCTTAAAACAAGTTTCAGTTTCAGTTCGTTGAAC
CGACCGCTAACCTACAGAGCAGTTGCCTAAAACACGGGTATTCTTACGAATC
ATTTACCGCTCGTAACTTTTGAGAATGAAAACTGTATTCGTTCTCTCTCGCTGCT
CTGCCTTTGCTGCTCAGTAAGCAGCTCGACCCCGGAGCTTTATTACGCTCCCGG
GAAACGCCAGTCTCTTTACGACTGGCCAGGTTCTACAATTACTGCGAGCCGTGTTA
CCCAGCACTCGCAACATTGACTTACGAGTGCCCCAGAAAAGAGCTGTTAAAGAT
TTTACCTTGCCCAGAAATTCGGGCGATCTGGGGAGGAGGGCTACAACGCCGCA
GAGAAATTTTCTCGCGGTGAAGCAGAGTTTAAAAAGTTCTTTCAGTATGGTG
TGCTGAAAGCGAGAGAAAAGCTACGGAGAGTTCCTAAAATCGATATTAGAATGAA
CCATATTATTATGGTCTTACGCGATATGGGCACTCTTATGCTGAGCTCGCTTTTGCTGGTACTTG
TTGAAGAACTATACCATAGAAATACTTATGCTGAGCTCGCTTTTGCGTTCACCAC
CTTTTTGGTGAAGCTCGATGGATTTTTGCGTAGGAAATTTAAATTAAATCCT
```

Beet intron

```
GGTTTATATGCTACTACTGCTGTGTTCACTGTTATTCAGGGGATCCTAGGCAAAAATCCATAC
ATTTCTGTTTCGTTTTCGTTCACTGTATTCAGGGATCCTAGGCAAAAATCCATAC
```

P15A4-P0 antisense

```
CACGAGCTTCACCAAAAGTGGTGAACGCAAAACGGAGCTCAGCATAAG
TATTTCTATGCTATAGTTCTTCAACAAGTACCACAGCGGTGCAAGAGTGCC
CATATCGGTAAGACCATAATAATAGTCCATTCTAATATCGATTTTAGGAC
TCTCCCGTAGCTTTCTCGCTTTCAGCACACACATACTGAAAGGAACTTTTA
AACTCTGCTTCACCGCAGAGAAATTTCTCTGCGCGTTGTAGCCTCTCCC
CCAGATCTCTGCCTGAATTTCGGCAAGCTAAAATCTTTTAACGCTCTTTCTG
GGGGGCACTCGTAAGTCAATGTTGCGAGTGCTGGGTAACACGGCTCGCAG
TAATTGTAGAACCTGGCCAGTCGTAAAGACTGAGCAGCAAAGCAGAGCAGCGA
TAAGCTCCACGGGGTCGAGCTGCTTACTGAGCAGCAAAGGCAGAGCAGCGA
GAAGAGAACGAATACAGTTTCATTCTCAAAAGTTACGAGCGGTAAATGATT
CGTAAGAAAATACCGCGTGTTTAAAACTCGCTCTGTAGCTGTAGCCGTCGG
TTCAACGAACAAGTGAACTTGTTTGTTTAAGCTGAAATTGCATAGACTGCT
AGATCCTGCTGTTTCTTTGTTATCTATGATACCAAACCAAACTATAGACAT
TAAACATATCATGAACAAAAACACCGCCAAACCAAACAATTCTAGATAATATATAAA
AATAGTTTCGGTGAGAGTCACAACGACCGTCACTTCACCCCTTTTACCATTAT
GTCAACATCGTCTCTTTGGTGGCAACCTTAGTGATGACTCGGCTACATGCTTTG
GAATATGTCCAACTCCAAATTGAGCAACGAATTCGCGGCCATGATCAGCCGCTC
CCCTTAAAATTGCTCCCGCATAGCTTGCGAGCGTTTAACATCGTTGCTGAAAACGGT
GAGTACAACATACTGACAACAACAATCAACCGGCAACTATGTACAATACAATATTAGAT
AAATCTACTTTAACCACAAGCACC
```

P0-P15A4 sense     Beet intron (91bp)     P0-P15A4 antisense

P0-P15A4 sense

```
CAAAGAACCAGCGAGGATCTAGCAGTCTATGCAATTTCAGCTTAAAACAAACA
GTTTCACTTGTTCGTTGAACGACCGCTAACAGCTAACAGAGCGAGTTTAAACAC
CGGTATTTTCTTACGAATCATTTACCGCTCGTAACTTTGAAGAATGAAAACTGTA
TTCGTTCTCTCTCGCTGCTCTGCCTTTGCTGCTCAGTAAGCAGCTCGACCCCGGG
AGCTTTATTTACGCTCCCGGAAACGCAGTCTTTACGACTGGCCAGGTTCTACA
ATTACTGGGGAGCCGTGTACCCAGCACTCGCCAACATTGACTTACGAGTGCCCC
CAGAAAAGACGTTAAAAGATTTTACCTTGCCGAAATTGCAGGCAGAGATCTGGG
GGAGAGGCTACAACGCCGCAGAGAAATTTTCTCTCGCGGTGAAGCAGAGTTTAA
AAAGTTCCTTTCAGTATGGTGTGCTGAAAGCGAGAGAAAGCTACGGGAGAGTCCT
AAATCGATATTAGAATGGACCATATTATTATGGTTCTTACGCGATATGGCACTC
TCTTGCACCGTCTGGTACTTGTTGAAGAACTATACCATAGAAATACTTATGCTGA
GCTGCTTTTGCGTTCACCCACTTTTTGGTGAAGCTCGTATGGATTTTG(AT)
GGTGCTTGTGGTTAAGTAGATTTATCTAATATGTATTGTACATAGTTGCCGGTTGTGT
TGTTGTCAGTATGTTGTACTCACCGTTTTTCAGCAACATGATGTTAAAGCGTCCAGCTATGC
GGGAGCAATTTTAAGGGGAGCGGCTGTATCAGCCGAGTCCATCCTAAGGTTGCCACCAAGA
GGAGTTGCCGATATTCCAAAGCATGTAGCCGAGTCCATCCTAAGGTTGCCACCAAGA
GCACGATGTTGACATAATGTAAAAGGGGTGAAGTGACCGTTCGTGTGACTCTCA
CCGAAACTATTTTATAATAATTATCTAGATGTTTCGGTTTGGCCGTGTTTTGTTCATGAT
ATGTTTAATGCTATAGTTTCGTTTCGTATCATAGATA4GCTAGGAAATTTAAATTAA
```

Beet intron

```
ATCCTGGTTTATATGTACTACTGTTGTAGCTGAAATTTAGTCTCTTCTGCTG
AATTTATTTCTGTTCGTTTCACTGTTATTCAGGGGATCCTAGGTTATCTATG
```

P0-P15A4 antisense

```
ATACCAAAACCAAACTATAGACATTAACATATCATGAACAAAACCCGCCAAACC
AACAATTCTAGATAATATTATAAAATAGTTTCGGTGAGAGTCACACACGACGGT
CACTTCACCCCTTTTACCATTATTGTCAACATCGTGCTCTTTGGTGGCAACCTTAGT
GATGGACTCGGCTACACTTCGTTGGAATATGCAACTCGCAAACTTGAGCAAACGAAT
TCGGGCCATGATACAGCCGCCGCCCCTTAAAATTGCTCCCGCATAGCTGGACGCT
TTAACATCGTTGCTGAAAACGGTGAGTACAACATACTGACAACAACACAACCGGC
AACTATGTACAATACAATATTAGATAAATCTACTTAACCACAAGCACC(AT)CAAAA
ATCCATACCACGAGCTTCACCAAAAGGTGCTGAACAAGTACCAGACGGTGCAAGA
GCATAAGTATTTCTATGGTATAGTTTCTTCTCAACAGTAATATGTCCATTCTAATATCGAT
GAGTGCCCATATCGCGTAAGACCATAATAATATGCCCACCACCATACTGAAAGG
TTTAGGACTCTCCCGTAGCTTCTCTCACCGCAGAGAAAATTTCTCGCGCGTTGTA
AACTTTTTAAAACTCTGTTCACCGCAGAGACTCGTAAAGACTGCCGTTTCCCGG
GCCTCTCCCCAGATCTGTCCTGCCTGAATTTCGGCAAGTAAATCTTTTAC
GTCTTTTCTGGGGGCACTCGTTAGTCAATGTTGCGAGTGCTGGTAACACG
GCTCCGCAGTAATTGTAGAACCTGGCCAGTCGTAAAGACTGCGTTTGCCCGG
GAGCGTAAATAAAGCTCCGGGTCGAGCTGCTTACGAGCAGCAAGCA
GAGCAGAGAAGAGAACGAATACAGTTTCATTCTCAAAAGTTACGAGCGG
TAATGATTCGTAAGAAATACGCCGTGTTTAAAACTCGCTCTGTAGCTGTT
AGCGGTCGGTTCAACGAACAAGTGAAACTGTTTGTTTTAAGCTGAAATTGCA
TAGACTGCTAGATCCTCGCTGGTTTCTTTTG
```

Fig. 10

P0 GENE SILENCING CONSTRUCTS AND USE

This application is a continuation of U.S. patent application Ser. No. 14/128,962, filed 27 Feb. 2014, which is a National Stage Application of PCT/EP2012/061436, filed 15 Jun. 2012, which claims benefit of Ser. No. 11171196.6, filed 23 Jun. 2011 in Europe and which applications are incorporated herein by reference. To the extent appropriate, a claim of priority is made to each of the above disclosed applications.

FIELD OF THE INVENTION

The present invention is related to a method for conveying viral resistance or tolerance to one or more virus(es), in particular to beet mild yellowing virus (BMYV) and to beet necrotic yellow vein virus (BNYVV) or to BMYV alone in a plant, in particular in a sugar beet plant. Furthermore, the present invention relates to the virus-resistant or -tolerant plant obtained according to this method, as well as to seeds and progeny derived therefrom.

The present invention also relates to gene silencing constructs, especially hairpin constructs mediating BMYV, or BMYV and BNYVV RNA silencing and their use.

BACKGROUND OF THE INVENTION

Plant viruses are a serious problem for many of the major agricultural crops, as virus infections cause large harvest losses.

In sugar beet, the major causes of diseases are: (i) yellowing caused by a polerovirus, the Beet mild yellowing virus (BMYV) transmitted by its principal vector *Myzus persicae* in a persistent manner; (ii) sugar beet rhizomania caused by a benyvirus, the Beet necrotic yellow vein virus (BNYVV), transmitted by *Polymyxa betae*. Extensive use of resistant against BNYVV permitted to preserve yields, however resistant breaking viral isolates are occurring and there is an urgent need for novel resistant varieties.

Fungus-transmitted viruses, such as BNYVV may be retained in resting spores in soil for years once a field becomes infested. As no effective chemical or physical methods exist for eliminating the virus, neither in the plants nor in the soil, the only option for the sugar beet farmer is the use of genetically resistant cultivars. Several companies have provided a number of tolerant, even partially resistant varieties through breeding. This is, however, a very tedious and time-consuming process, generally taking a long time before useful resistant plants are obtained.

The rapid revolution in the areas of plant engineering has led to the development of new strategies to confer genetic resistance to viruses. Resistance to viral diseases through the introduction of portions of viral genome sequences whereby the viral sequence (construct) is transformed into a plant cell and a plant, has become a new source of resistance.

Sugar beet is known to be recalcitrant species in genetic engineering, complicating a possible successful induction of viral resistance.

A few examples of engineering tolerance, for instance to the BNYVV by transforming and expressing the BNYVV coat-protein sequence in the sugar beet genome, have been published (W091/13159) though there are only rare report data on whole functional transgenic sugar beet plants, such as those disclosed in EP 1 169 463 B1. In particular, reports show limited data on the level of resistance observed in infected conditions with transgenic sugar beet plants transformed with a gene encoding a BNYVV coat-protein sequence.

The genome of beet necrotic yellow vein furovirus (BNYVV) consists of five plus-sense RNAs, two of which (RNAs 1 and 2) encode functions essential for infection of all plants while the other three (RNAs 3, 4 and 5) are implicated in vector-mediated infection of sugar beet (*Beta vulgaris*) roots. Cell-to-cell movement of BNYVV is governed by a set of three successive, slightly overlapping viral genes on RNA 2 known as the triple gene block (TGB), which encode, in order, the viral proteins P42, P13 and P15 (gene products are designated by their calculated Mr in kilodalton).

The genome of BMYV consists of a linear plus-sense RNA with six major open reading frames (ORFs 0-5). ORFs 1 and 2 encode proteins involved in virus replication, while each of the other three ORFs (ORFs 3, 4 and 5) codes for structural proteins (major and minor coat proteins) and a putative movement protein.

It has been shown that P0 protein of BMYV has a poor expression, a consequence of unfavorable initiation codon context of the P0 AUG and a strong tendency to maintain a low expression. Furthermore, this part of the genome is highly variable, and this sequence diversity has been exploited to discriminate the different species.

Diseases caused by BNYVV are shown to expand geographically, at a speed depending upon the combination of numerous local environmental and agricultural factors. Therefore there is a need to improve the genetic resistance mechanisms which may, alone or in combination, confer a stable and long lasting resistance of sugar beet plants which are grown for industrial use.

STATE OF THE ART

The patent application WO 2007/128755 discloses a TGB-3 sequence used to reduce and/or suppress the deleterious effects of wild type TGB-3 in plants, in order to generate virus-resistant transgenic plants especially sugar beets resistant to Beet necrotic yellow vein virus.

Carmen Simon-Mateo et al., Biochimica et Biophysica Acta, 1809 No. 11-12, pages 722-731, 2011, discloses different anti-viral strategies used to obtain viral resistant plants in the last 25 years.

A. Kozlowska-Makulska et al., Journal of General Virology Vol. 91, No. 4, pages 1082-1091, 2010, discloses the RNA silencing suppressor activity of P0 proteins from different isolates of the beet-infected poleroviruses beet chlorisis virus and beet mild yellowing virus.

Pu Yan et al. Journal of Virological Methods Vol. 166, No. 1-2, pages 101-105, 2010, discloses RNA silencing constructs to develop virus-resistant plants through expression of virus-derived hairpin RNAs.

SUMMARY OF THE INVENTION

The present invention provides methods and means to confer viral tolerance or resistance that do not present the drawbacks of the state of the art, preferably methods and means that confer tolerance, resistance, preferably extreme or total resistance, especially BMYV (Beet mild yellowing virus) viral tolerance or resistance (including extreme or total BMYV resistance) or preferably combined BMYV (Beet mild yellowing virus) and BNYVV (Beet necrotic yellow vein virus) tolerance or resistance (including extreme or total BMYV and BNYVV resistance) in a plant cell or in a plant, in particular in a sugar beet plant cell or in a sugar beet plant (possibly generated from this plant cell).

The present invention further provides genetically modified or transformed plant cells obtainable as such, or obtained from this method, and that may be generated into plants that exhibit these increased tolerance or resistance to the mentioned plant viruses.

The invention also provides progeny, i.e. virus tolerant or virus resistant progeny, seeds or other reproducible organs or structures originating from this transformed plant or plant cells.

A first aspect of the present invention is a RNA construct comprising a sense segment sequence and an antisense segment sequence having sequences deduced from P0 gene (or from the gene encoding BO protein) of BMYV genome or from an ortholog gene, wherein said sense segment and said antisense segment sequences both comprise a nucleotide fragment having sequence sharing at least 85% of sequence identity with the P0 gene from BMYV genome or from an ortholog gene.

Preferably, in this RNA construct, the sense segment and/or antisense segment sequence(s) further comprise(s) a nucleotide fragment having sequence(s) sharing at least 85% of sequence identity with the 5'-end untranslated sequence (5' UTR) adjacent to the P0 gene nucleotide sequence.

More preferably in this RNA construct, the sense segment and antisense segment sequences comprise a nucleotide fragment having sequences sharing at least 85% of sequence identity with the P0 gene from BMYV genome.

Advantageously, in this RNA construct, the sense segment and antisense segment sequences further comprise a nucleotide fragment having sequences sharing at least 85% of sequence identity with PI gene of BMYV genome.

Possibly, in these RNA constructs, the sense segment comprises or consists of the sequence SEQ.ID.NO:1 and/or the antisense segment comprises or consists of the sequence SEQ.ID.NO:3.

Advantageously, in these RNA constructs, the sense segment and antisense segment sequences further both comprise a nucleotide fragment sharing at least 85% of sequence identity with the BNYVV genome.

A related aspect of the present invention is a DNA construct transcriptable into this (these) RNA construct(s).

Another related aspect is a vector comprising the nucleotide sequence of these (DNA) nucleic acid constructs.

Another related aspect is a double stranded self-complementary RNA molecule expressed by these DNA construct or vector.

The present invention also relates to a method for inducing tolerance or resistance, preferably total resistance to at least the BMYV virus and possibly another virus, in a plant or a plant cell, the said method comprising the steps of: preparing the nucleic acid construct of the present invention (e.g. comprising a sequence deduced from P0 gene and/or of BMYV genome), operably linked to one or more regulatory sequence(s) active in the plant or the plant cell, and transforming the plant cell with the nucleic acid construct, thereby inducing resistance to at least the BMYV virus in the plant or in the plant cell.

Advantageously, this method further induces tolerance the another virus, which is selected from the group consisting of the Turnip yellows virus, Curcubit aphid-borne yellows virus, Potato leafroll virus, Sugarcane yellow leaf virus, Pea Enation Mosaic Virus, Beet western yellows virus-USA, Beet chlorosis virus, Cereal yellow dwarf virus and BNYVV virus, preferably the BNYVV virus.

A related aspect is a method for inducing tolerance to at least the BMYV virus comprising the step of preparing a nucleic acid construct comprising a sense and an antisense segments deduced from BNYVV nucleotide sequence, being preferably deduced from the gene encoding the P15 protein of the said BNYVV.

Still a related aspect is the use of a nucleotide sequence comprising a sequence deduced from P0 gene and/or of BMYV genome and/or of the RNA, DNA or vector of the present invention for inducing tolerance or resistance, preferably total resistance to BMYV virus and/or to BNYVV virus, in a plant or a plant cell.

Another aspect is a transgenic plant or a transgenic plant cell tolerant or resistant, preferably totally resistant to at least the BMYV virus and possibly one or more other(s) virus(es) and comprising a nucleic acid construct able to express the nucleotide sequence of the present invention (comprising a sequence deduced from P0 gene and/or from BMYV genome), operably linked to one or more regulatory sequence(s) active in the plant or the plant cell, comprising the vector of the present invention, or comprising a double stranded self-complementary RNA molecule of the present invention.

Preferably, this transgenic plant or transgenic plant cell is resistant to another virus, which is selected from the group consisting of the Turnip yellows virus, Curcubit aphid-borne yellows virus, Potato leafroll virus, Sugarcane yellow leaf virus, Pea Enation Mosaic Virus, Beet western yellows virus-USA, Beet chlorosis virus, Cereal yellow dwarf virus and BNYVV virus, preferably the BNYVV virus.

Preferably, this transgenic plant or transgenic plant cell is selected from the group consisting of lettuce, cucumber, potato, sugarcane, pea, barley and sugar beet, being preferably a sugar beet or a sugar beet cell.

A related aspect is a transgenic plant tissue and/or reproducible structure derived from this transgenic plant cell (according to the present invention), wherein said tissue is selected from the group consisting of fruit, stem, root, tuber, and seed or wherein said reproducible structure is selected from the group consisting of calluses, buds or embryos.

SHORT DESCRIPTION OF THE DRAWINGS

FIGS. 1A and B represent a fragment of viral P0 sequence according to the invention (FIGS. 1A and B; SEQ. ID. O: 13) with a sense P0 nucleotide sequence (SEQ. ID. NO: 1, shorter than the whole P0 sequence SEQ ID NO: 17) and a corresponding homologous antisense P0 nucleotide sequence (bold, SEQ. ID. NO: 3) interspersed with a *petunia* intron sequence of 1352 bp (bold underlined, SEQ. ID. NO: 11). A few nucleotides in Figure IB are indicated in bold italic. These correspond to the 5' UTR of the viral BMYV genome. Other few nucleotides in italic and underlined in Figure D3 and do not belong to P0 nor to the intron, but are still present as these are the remains of the cloning strategy. A construct comprising the full hairpin (SEQ. ID. NO: 13) is also referred to as hpP0 construct 1.

FIG. 2 (A and B) represents another fragment of viral P0 sequence according to the invention (FIGS. 2A and B; SEQ. ID. NO: 14) with a sense P0 nucleotide sequence and an antisense P0 nucleotide sequence (bold) interspersed with a beet intron sequence of 91 bp (bold underlined, SEQ. ID. NO: 12). A few nucleotides in FIG. 2B are indicated in bold italic. These correspond to the 5' UTR of the viral BMYV genome. Other few nucleotides in italic and underlined in FIG. 2B that neither belong to P0 nor belong to the intron, are still present as these are the remains of the cloning strategy. The sense and antisense P0 nucleotide sequences herein are the same as those given in Figure IB. A construct comprising the full hairpin (SEQ. ID. NO: 14) is also referred to as hpP0 construct 2.

FIG. 3 highlights the differences in the 5'-end of SEQ. ID. NO: 1 compared to the 5'-end of the P0 BMYV coding sequence represented by SEQ ID NO: 17. The underlined sequence of FIG. 3 corresponds to the non-functional 5' leader sequence of SEQ. ID. NO: 1.

Figure 4B:
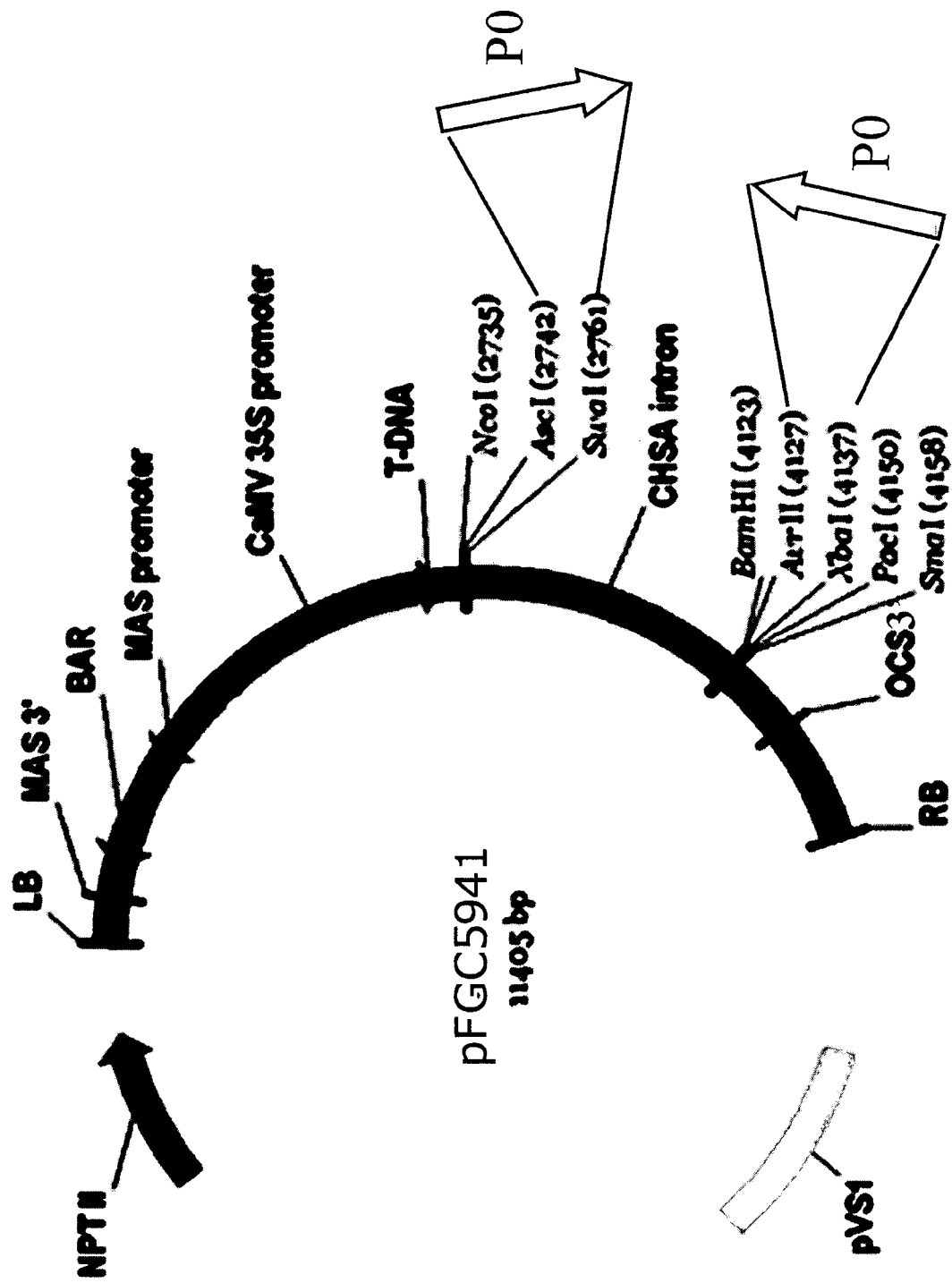

FIG. 4 (A and B) is a schematic representation of the pFGC5941 vector into which a fragment of P0 gene was introduced in sense (SEQ. ID. NO: 1) and antisense (SEQ. ID. NO:3) orientation, interspersed either by an intronic sequence of the Chalcone Synthase A gene of petunia (CHSA; SEQ. ID. NO: 11) (FIG. 4A, pFGC5941, construct 1; SEQ. ID. NO:13), or interspersed by a beet intronic sequence (SEQ. ID. NO: 12) of 91 nt (FIG. 4B, pFGC5941, construct 2; SEQ. ID. NO:14). CaMV 35S promoter: promoter 35S of CaMV; OCS 3': polyadenylation signal of the octopine synthase gene; MAS promoter: promoter of the mannopine synthase gene; MAS 3': polyadenylation signal of the mannopine synthase gene; BAR: Basta herbicide resistance gene; pVS1: replication origin of pVS1; NPTII: Kanamycine resistance gene; LB, RB: left and right T-DNA borders.

Figure 5:
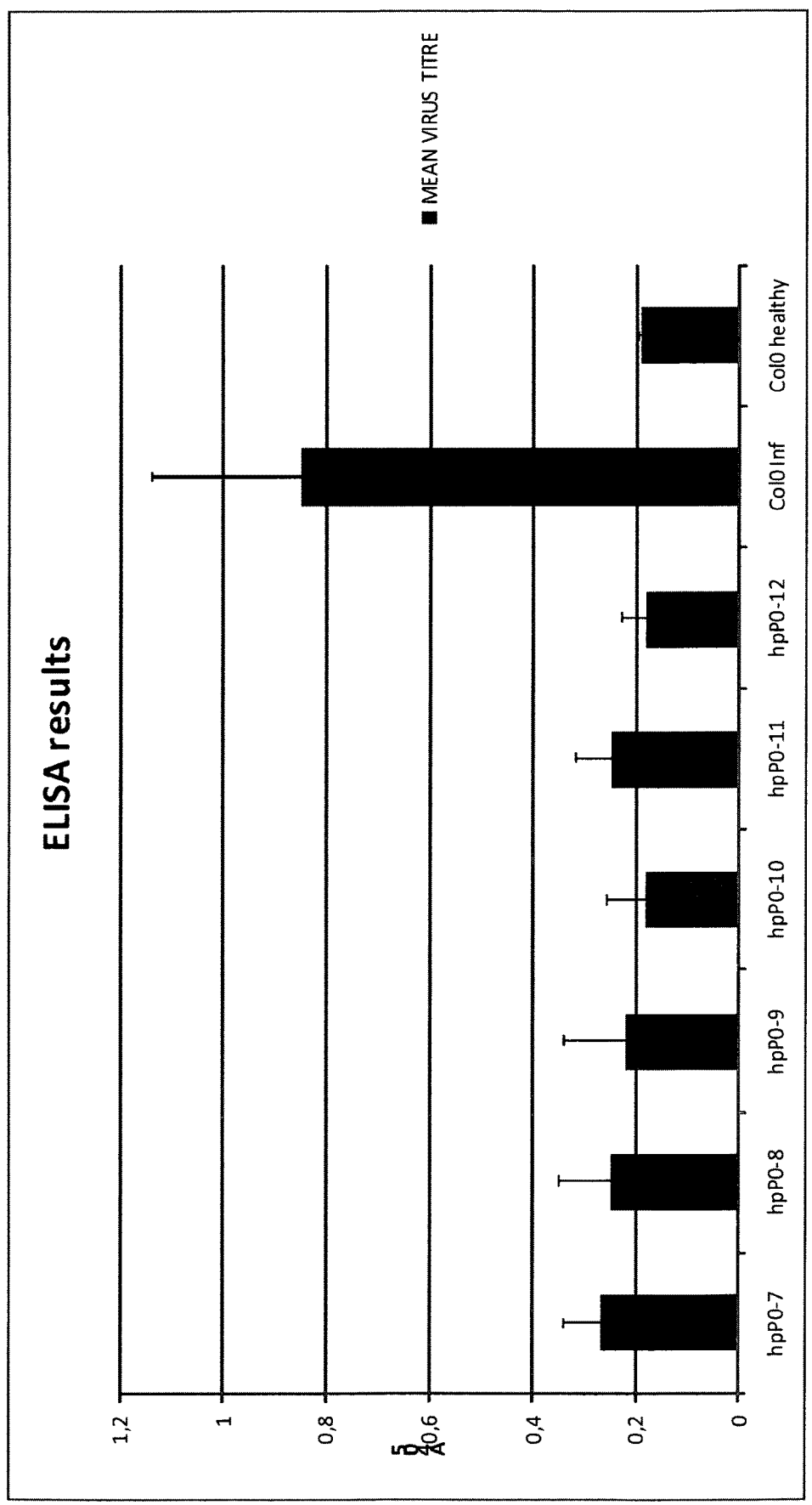

FIG. 5 is a statistical analysis of the resistance test obtained with construct 1 (hpP0u with the petunia intron). Each histogram represents the mean BMYV titre with standard error on 10 BMYV-inoculated plants (Y). hp: hairpin; Inf: infected. In the Y axis: optical density ($A_{405}$) obtained by ELI SA 0, 0.2, 0.4, 0.6, 0.8, 1, 1.2. In the X axis, from left to right: transgenic lines: hpP0-7, hpP0-8, hpP0-9, hpP0-10, hpP0-11 and hpP0-12; BMYV-infected control: Co10 Inf; Co10 healthy.

Figure 6:
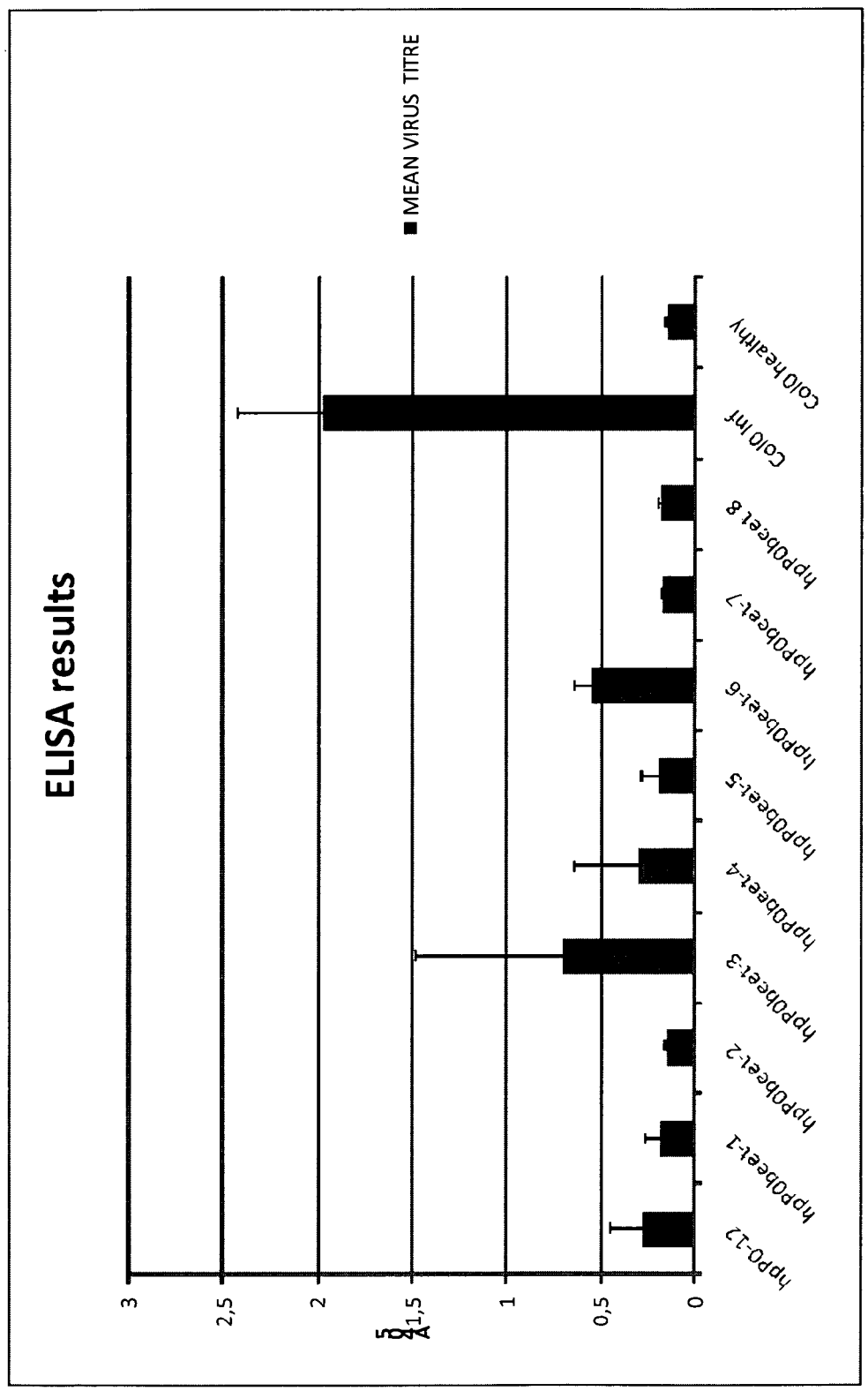

FIG. 6 is a statistical analysis of the resistance test obtained with construct 2 (hpP0u with the beet intron). Each histogram represents the mean BMYV titre with standard error on 10 BMYV-inoculated plants (Y). hp: hairpin; hpP0: construct 1; hpP0beet: construct 2; Inf: infected. In the Y axis: optical density (A405) obtained by ELISA 0, 0.5, 1, 1.5, 2, 2.5, 3. In the X axis, from left to right: transgenic lines: hpP0-12 (construct 1), hpP0beet-1 (construct 2), hpP0beet-2, hpP0beet-3, hpP0beet-4, hpP0beet-5, hpP0beet-6, hpP0beet-7 and hpP0beet-8; BMYV-infected control: Co10 Inf; Co10 healthy.

Figure 7:
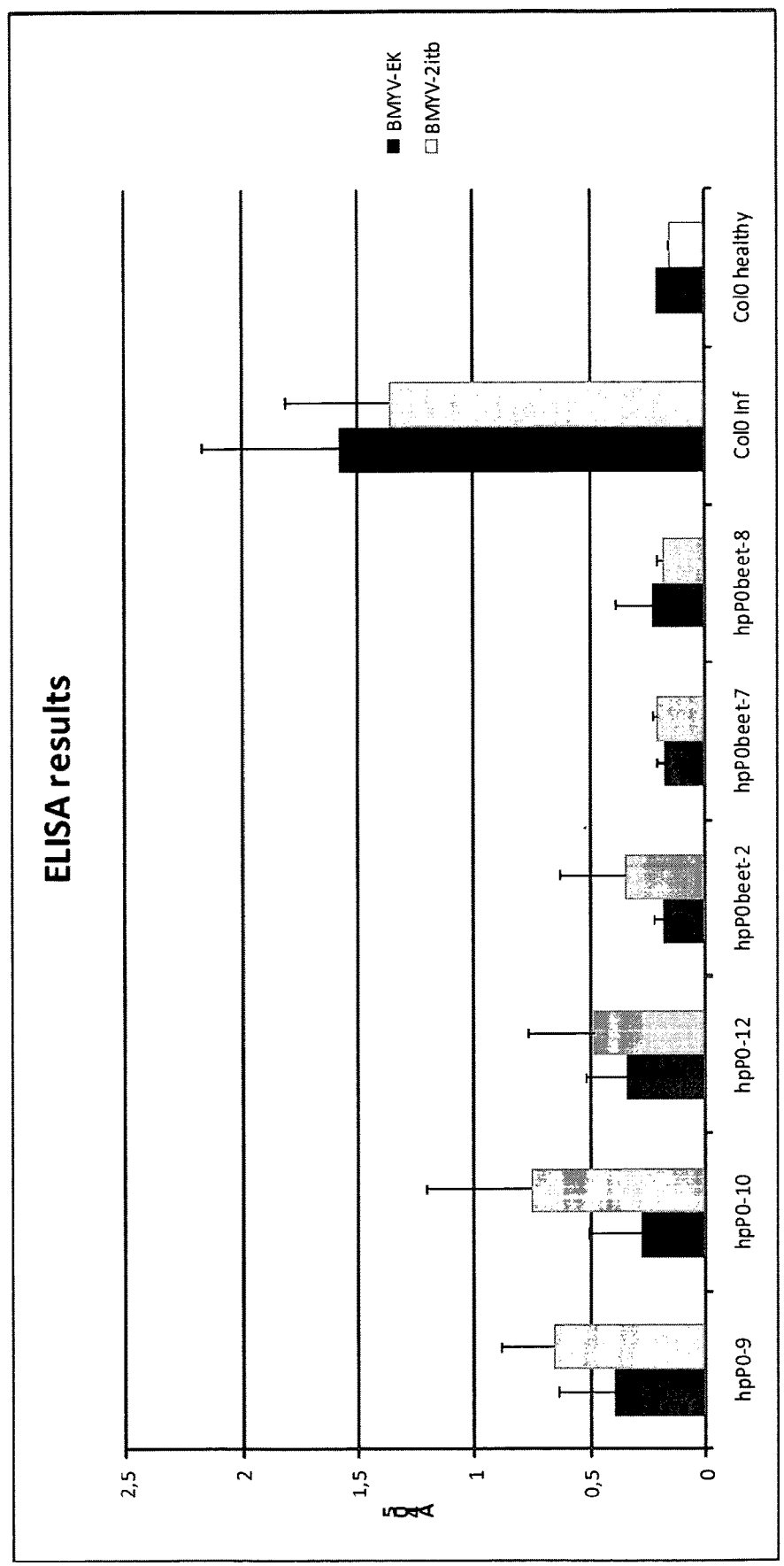

FIG. 7 is a statistical analysis of the resistance test obtained with constructs 1 and 2 respectively. Each histogram represents the mean virus titre with standard error on 10 inoculated plants (Y). The histograms with dark grey Co10ur represent the infection by BMYV-EK clone and the histograms with light grey, the infection by BMYV-2itb isolate by aphid transmission method respectively. hp: hairpin; hpP0: construct 1; hpP0beet: construct 2; Inf: infected. In the Y axis: optical density (A405) obtained by ELISA 0, 0.5, 1, 1.5, 2, 2.5. In the X axis, from left to right: transgenic lines: hpP0-9 (construct 1), hpP0-10, hpP0-12, hpP0beet-2 (construct 2), hpP0beet-7 and hpP0beet-8; infected control: Co10 Inf; Co10 healthy.

FIG. 8 represents the WT P0 sequence (SEQ. ID. O: 17 and 18).

FIG. 9 (A and B) represents the sequence of the hairpin construct hpP15A4-P0 according to the invention (FIGS. 9A and B, SEQ. ID. O: 15) with a sense P15A4-P0 nucleotide sequence (SEQ. ID. NO: 7), italic nucleotides for P15A4 sequence with the 3 mutations underlined and usual nucleotides for P0 sequence; compared to WT P15: A is replaced by C and AG by GC.) and SEQ. ID. NO: 8 corresponding to an antisense P15A4-P0 nucleotide sequence (bold italic for P15A4 and bold for P0) interspersed with a beet intron sequence of 91 bp (bold underlined, SEQ. ID. NO: 12). A few nucleotides in FIG. 9B are indicated in bold italic and underlined. These correspond to the 5' UTR of the viral BMYV genome. Other few nucleotides underlined in FIG. 9B that neither belong to P15A4-P0 nor belong to the intron, are still present as these are the remains of the cloning strategy. A construct comprising the full hairpin (SEQ. ID. NO: 15) is also referred to as hpP15A4-P0 construct 1.

FIG. 10 (A and B) represents the sequence of the hairpin constructs hpP0-P15A4-A and hpP0-P15A4-B according to the invention (FIGS. 10A and B, SEQ. ID. NO: 16) with a sense P0-P15A4 nucleotide sequence (SEQ. ID. NO: 9, usual nucleotides for P0 sequence and italic nucleotides for P15A4 sequence with the 3 mutations underlined) and SEQ. ID. NO: 10 corresponding to an antisense P0-P15A4 nucleotide sequence (bold for P0 and bold italic for P15A4) interspersed with a beet intron sequence of 91 bp (bold underlined, SEQ. ID. NO: 12). The difference between the two hairpin constructs is the presence of two additional nucleotides in P15A4 sequence (boxed nucleotides) for the hpP0-P15A4-B construct. A few nucleotides in FIG. 10B are indicated in bold italic and underlined. These correspond to the 5' UTR of the viral BMYV genome. Other few nucleotides underlined in FIG. 10B that neither belong to P0-P15A4 nor belong to the intron, are still present as these are the remains of the cloning strategy. A construct comprising the full hairpin (SEQ. ID. NO: 16) is also referred to as hpP0-P15A4-A construct 2 and as hpP0-P15A4-B construct 3.

Figure 11A:
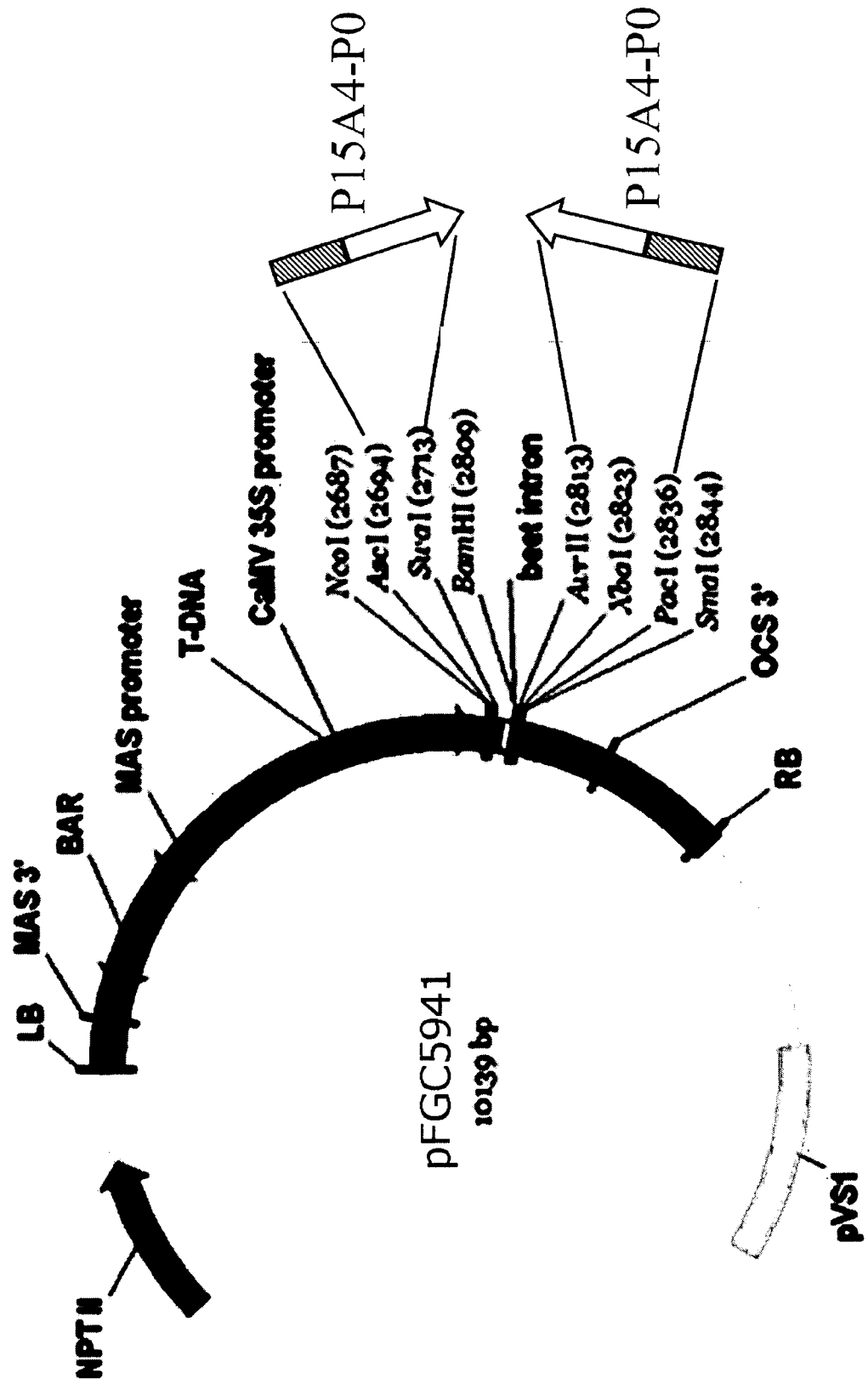
Figure 11B:
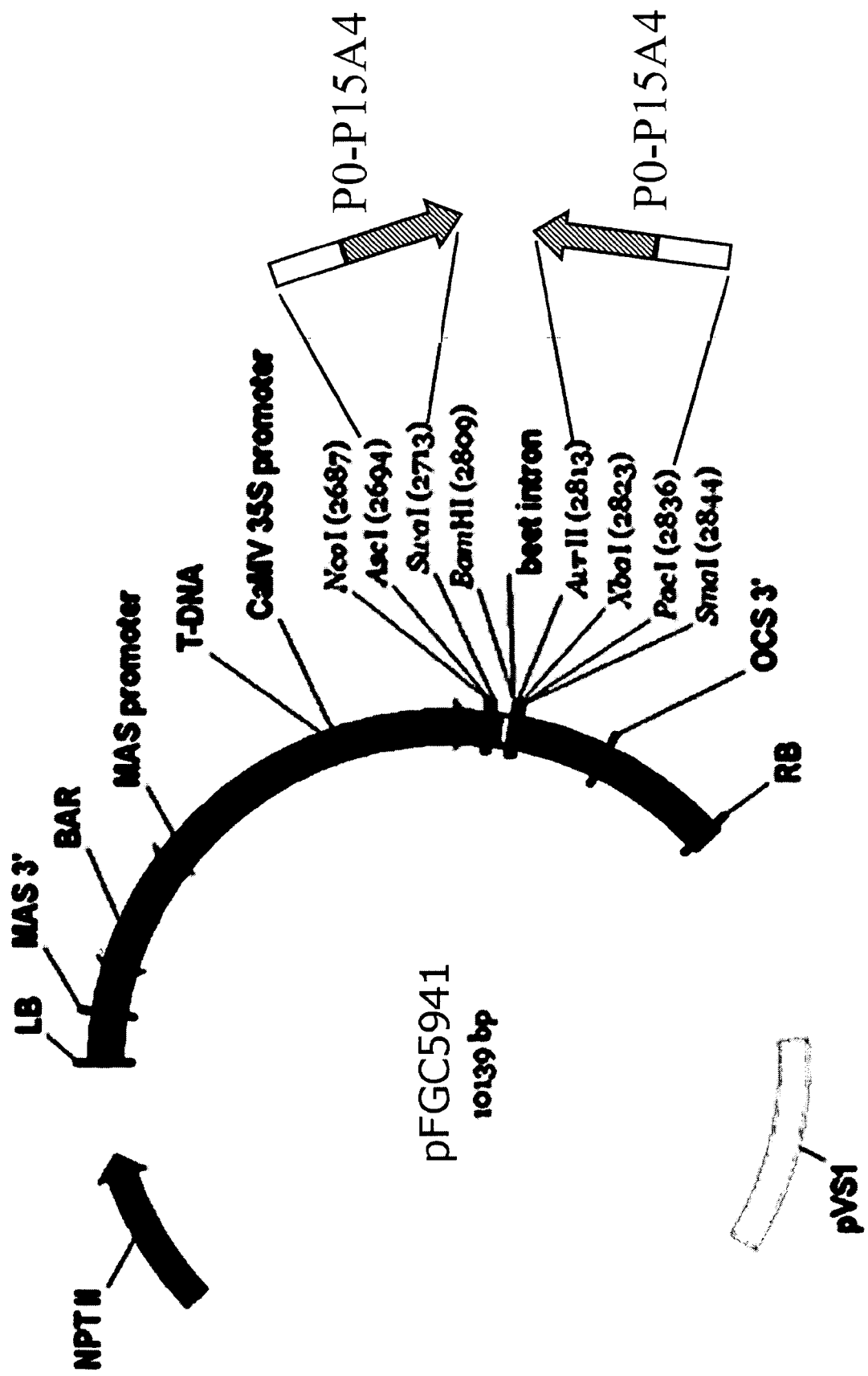

FIG. 11 (A and B) is a schematic representation of the pFGC5941 vector into which a P15A4-P0 sequence or P0-P15A4 sequence was introduced in sense and antisense orientation, interspersed by a beet intronic sequence of 91 nt (FIG. 11A, pFGChpP15A4-P0, construct 1 and FIG. 11B, pFGChpP0-P15A4-A and pFGChpP0-P15A4-B, construct 2 and 3 respectively). CaMV 35S promoter: promoter 35S of CaMV; OCS 3': polyadenylation signal of the octopine synthase gene; MAS promoter: promoter of the mannopine synthase gene; MAS 3': polyadenylation signal of the mannopine synthase gene; BAR: Basta herbicide resistance gene; pVS1: replication origin of pVS1; NPTII: Kanamycine resistance gene; LB, RB: left and right T-DNA borders.

DETAILED DESCRIPTION OF THE INVENTION

Considering the occurrence of both viruses within sugar beet growing areas, the inventors have developed transgenic plants that are resistant towards one or both (BMYV and/or BNYVV) viruses, or even additional viruses able to infect the same plant.

Indeed, BNYVV is a major concern and the inventors anticipate that BMYV prevalence also risks to grow.

A first aspect of the present invention is related to a RNA construct (such as a hairpin RNA preferably described hereafter as hpP0) comprising sense (RNA) segment and antisense (RNA) segment (both) having sequences deduced (i.e. sharing at least 85% of sequence identity) from P0 gene (or nucleotide sequence) or from the gene (nucleotide sequence encoding B0 protein) of BMYV genome or from orthologs genes or having sequences deduced (i.e. sharing at least 85% of sequence identity) from BMYV genome.

Advantageously, this (hairpin; hpP0) RNA construct comprises a sense (RNA) segment and an antisense (RNA) segment (both) further comprising (RNA) (sense and/or antisense) fragments deduced (i.e. sharing at least 85% of identity) from the 5'-untranslated (5'-UTR) region of BMYV (adjacent to this gene encoding P0 of BMYV or orthologs genes) and/or this (hairpin) RNA construct comprises a sense RNA segment and an antisense RNA segment having sequences deduced from both a nucleotide fragment of the 5'-UTR and from a (an adjacent) nucleotide fragment of the P0 nucleotide sequence of BMYV or of orthologs genes.

Preferably, these fragments of the 5'-UTR and of the P0 nucleotide sequence are adjacent in the BMYV genome.

This RNA hairpin, when comprising a fragment of the 5'UTR and of P0, is preferably referred in the present invention to hpP0u nucleotide sequence.

Possibly (but less preferably), this (hpP0 and/or hpP0u (RNA) hairpin(s)) construct(s) according to the invention do not comprise a fragment having a sequence deduced from another virus, such as BNYVV genome.

Advantageously, these RNA (hairpin; hpP0 and/or hpP0u) construct(s) according to the invention comprises a sense RNA segment and an antisense RNA segment further having (a fragment being) sequences deduced from the BNYVV genome, preferably in addition to the 5'UTR sequence from BMYV genome (adjacent to P0) and/or these RNA (hairpin; hpP0 and/or hpP0u) construct (s) comprises a sense RNA segment and antisense RNA segment (comprising a fragment having sequence deduced from P0 gene) both further comprising a nucleotide fragment sharing at least 85% of sequence identity with (a part of) the BNYVV genome.

More preferably, this sense and antisense RNA segments deduced from the BNYVV genome are sense and/or antisense sequences corresponding to (a part of) the P15 sequence of the BNYVV genome (when it is a hairpin, there are here below referred to hpP0-P15 or hpP0u-P15, the latter further containing a nucleotide fragment deduced from the 5' UTR sequence of the BMYV genome).

Advantageously, this hpP0 and/or hpP0u RNA (hairpin) construct(s) also comprises a sense and antisense nucleotide (RNA) fragments having sequences deduced from PI nucleotide sequence of BMYV.

In the context of the present invention, 'orthologs' refer to genes in different species that retain the same function (e.g. in the course of evolution). An example of ortholog genes of P0 gene (or nucleotide sequence) of BMYV genome is provided at table 1.

TABLE 1 non-exhaustive list of identified P0 sequence orthologs

| Virus | Size of P0 | Host |
|---|---|---|
| Turnip yellows virus (formerly BWYV-FL1) | 27.5 kDa | lettuce |
| Curcubit ephid-borne yellows virus | 26.4 kDa | cucumber |
| Potato leafroll virus | 27.2 kDa | potato |
| Sugarcane yellow leaf virus | 28.3 kDa | sugarcane |
| Pea Enation Mosaic Virus | 34 kDa | pea |
| Beet western yellows virus-USA | 26.3 kDa | sugar beet |
| Beet chlorosis virus | 27.4 kDa | sugar beet |
| Cereal yellow dwarf virus | 28.3 kDa | barley |

In the context of the present invention, the term "segment" refers to a nucleotide (RNA) sense and/or antisense nucleotide sequence(s) able to be used in gene silencing. A segment can therefore be as short as 10 (preferably at least 15, 16, 17, 18, 19, 20, 21, 22, 23, 24, 25, 30, 35 or 40) nucleotides, but can also span over several genes and/or genes and adjacent (5') untranslated regions (5'UTR). The preferred segment spans over (the 5' part of) P0 gene (or nucleotide sequence) and the adjacent 5'UTR.

In the context of the present invention, the term "fragment" refers to a nucleotide (RNA) sense sequence and/or antisense nucleotide sequence having a sequence deduced from a target viral nucleotide sequence. A fragment can therefore be as short as 10 (preferably at least 20, 21, 22, 23, 24, 25, 30, 35 or 40) nucleotides, but can also span over more than a gene.

In the context of the present invention, possibly, several fragments are associated to form a (RNA) sense and/or antisense segment(s).

Possibly (especially in the case of two fragments deduced from the genome of different viruses are associated), the fragments are associated via a linker or spacer (not derived from the target viral sequence) sequence to form a (RNA) sense segment and/or an (RNA) antisense segment(s).

Preferably, in the present invention, the 5'UTR fragment and the adjacent P0 fragment are associated without a linker or a spacer sequence.

These constructs may comprise modified sequences (mutated sequences).

Therefore, the term "sequence deduced" refers to nucleotide sequences having at least 85% (more preferably, at least 86%, 87%, 88%, 89%, 90%, 91%, 92%, 93%, 94%, 95%, 96%, 97%, 98%, 99% or even 100%) of sequence identity with the mentioned gene. For instance a sequence deduced from P0 gene (or sequence) of BMYV genome refers preferably to a nucleotide sequence having at least 85% of sequence identity with the sequence SEQ. ID. NO: 17.

Preferably, these constructs do not contain more than 15% of mutated residues by comparison to the wild-type sequence (SEQ. ID. NO: 17) and/or to the sequence SEQ. ID. NO: 1 or the sequence SEQ. ID. NO: 3.

Advantageously, these (RNA) constructs (including segments and, more preferably fragments) have a size higher than about 25 nucleotides, preferably higher than about 50 nucleotides.

Possibly, these (RNA) constructs (in the form of sense segment and/or of antisense segment) have a size lower than about 10000 nucleotides, possibly lower than about 5000, about 3000, about 2000 or about 1000 nucleotides.

Preferably, the sense (RNA) segment and/or the antisense (RNA) segment (having sequence deduced from the 5'UTR of P0) comprise fragment(s) that spans over at least 5 nucleotides, more preferably at least 10 nucleotides, still more preferably at least 20 nucleotides of the 5'UTR (adjacent to the P0 gene), but possibly over less than 40 nucleotides and preferably over less than 30 nucleotides of this 5'UTR (adjacent to the P0 gene).

The molecular characterization of the plant material demonstrated the presence of small RNA molecules complementary to both sense and antisense of the BMYV P0 sequence, indicating that the silencing mechanism was obtained and triggered the degradation of the genomic RNA.

These RNA (hairpin) constructs efficiently trigger PTGS, targeting the degradation of the transcribed RNA of BMYV (or of both BMYV and BNYVV).

The inventors have indeed found a more potent inhibition of BMYV (and of BNYVV) by the constructions harbouring a 5'UTR of BMYV, in addition to P0 (possibly in addition to (fragments) sequences deduced from the BNYVV genome).

For instance, when using the hpP0-P15 nucleotide construct, the inventors noticed the production of siRNAs targeting the BMYV sequence, but also the BNYVV RNA2 sequence, resulting into a very efficient and unexpected inhibition of both viral infections.

In the case of this double construct, the inventors noticed a more pronounced reduction of both viral infections (BMYV and/or BNYVV) than if using a comparable construct targeting exclusively BNYVV or BMYV.

A related aspect is a RNA construct (such as a hairpin RNA) comprising sense (RNA) segment and antisense (RNA) segment (both) having sequences deduced (i.e. sharing at least 85% of sequence identity) from BMYV genome (or nucleotide sequence thereof).

Preferably, the RNA construct (such as a hairpin RNA) deduced from BMYV genome comprising sense (RNA) segment and antisense (RNA) segment has a sense sequence deduced (i.e. sharing at least 85% of sequence identity) from the 5'-half of the BMYV genome and/or form the group consisting of nucleotides of BMYV genome encoding P0, PI, P2, P3, P4 and P5 proteins, more preferably from the nucleotides of BMYV genome encoding PI or P2 proteins.

Advantageously, these (RNA) constructs deduced from BMYV genome (including segments and, more preferably fragments) have a size higher than about 25 nucleotides, preferably higher than about 50 nucleotides.

Possibly, these (RNA) constructs deduced from BMYV genome (in the form of sense segment and/or of antisense segment) have a size lower than about 10000 nucleotides, possibly lower than about 5000, about 3000, about 2000 or about 1000 nucleotides.

Conversely, the inventors tested the effect of RNA constructs (in the form of hairpins) having a sequence deduced exclusively from BNYVV genome (such as the sequence encoding the P15 protein) or from BMYV genome.

These hairpin P15 constructs deduced from BNYVV resulted into a reduced BNYVV infection in plants co-infected by both viruses (by comparison to control constructs), but also induced some reduction of BMYV symptoms (by comparison to control constructs).

These hairpin hpP0 and especially hpP0u constructs deduced from BMYV resulted into a reduced BMYV infection in plants co-infected by both viruses (by comparison to control constructs), but also induced reduction of the symptoms due to BNYVV infection (by comparison to control constructs).

Two BMYV nucleotide sequences were tested as hpP0u nucleotide construct (sequence SEQ. ID. NO: 13 or 14).

The nucleotide sequence of SEQ. ID. NO: 1, 13 or 14 can be compared to the sequence SEQ. ID. NO: 17, which is the sequence of the wild type P0 nucleotide (see FIG. 8). The length of the sequence SEQ. ID. NO: 1 is shorter than the nucleotide sequence of the sequence SEQ. ID. NO: 17 (659 nt versus 720 nt) and it contains the 5'UTR of the viral genome (underlined nucleotides) except the first 5' end nucleotide.

Advantageously, the sense and antisense P0 nucleotide sequence are comprised into one molecule, and/or the sense P0 RNA segment and the antisense P0 RNA segment are comprised into one single RNA molecule. Advantageously, the RNA molecule according to the invention is capable of folding such that said RNA segments comprised therein form a double-stranded hairpin RNA molecule.

As used herein "hairpin RNA" refers to any self-annealing double stranded RNA molecule. In its simplest representation, a hairpin RNA consists of a double stranded stem made up by the annealing RNA strands, connected to a single stranded RNA loop. However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software, such as FOLDRNA.

Alternatively the sense and antisense P0 nucleotide sequences may be present (or encoded) in or on two separate molecules or nucleotide sequences, which may be administered or provided to a plant cell simultaneously and/or consecutively, so that, when transcribed, a double-stranded RNA molecule can form by base-pairing.

The present invention is also related to a DNA construct transcriptable into the RNA construct(s) of the invention and to a vector comprising this DNA construct, in particular an expression (and/or self replicating vector (such as a plasmid or a viral vector)) vector or expression cassette (or system), preferably encoding a sense and an antisense RNA segments having sequences deduced from the P0 sequence(s), operably linked with one or more regulatory sequences (promoter or operator sequence, including a polyA sequence), active into a plant or a plant cell, preferably into a specific tissue (preferably the root) of the plant.

Another aspect of the present invention relates to a transgenic plant or plant cell, such as *Arabidopsis thaliana* or sugar beet plant (*Beta vulgaris*) that is transformed with the nucleotide (DNA) construct, the vector and/or the RNA molecule according to the invention.

Advantageously, there is low, and even no, viral amplification in inoculated plant transformed with the fragment(s) of P0 nucleotide sequence(s) according to the invention.

Preferably, the DNA sequences according to the invention are stably integrated in the genome of the plant cell being transformed with the genetically modified P0 viral sequences according to the invention and/or with a vector comprising these sequences.

Alternatively, the transgene comprising a genetically modified P0 nucleotide sequence according to the present invention may be located on an episome or a self-replicating vector. Examples of self-replicating vectors are viruses, in particular gemini viruses or plasmids.

Numerous transformation vectors available for plant transformation are known to those of ordinary skill in the art, and the DNA or nucleotide constructs according to this invention (comprising the genetically modified P0 viral sequence) can be used in conjunction with any such vectors. The selection of vector depends upon the preferred transformation technique.

The components of the expression system may be modified, for instance to increase expression of the sense and antisense RNA segments.

The promoter operably linked to the sense and/or antisense nucleotide sequences according to the invention may be a native promoter of the cell to transform. The promoter alternatively can be a heterologous promoter, for example a tissue specific promoter, a developmentally regulated promoter, a constitutive promoter or an inducible promoter. Appropriate promoters are well known to person skilled in the art. In the present invention strong heterologous promoters that are active in root tissues or are primarily active therein (when expression in other tissues is not desired) are preferred.

A variety of transcriptional terminators are available for use in expression cassettes. These are responsible for the termination of transcription beyond the transgene and its correct poly-adenylation. Appropriate transcriptional terminators are those that are known to function in plants and include the CaMV 35S terminator, the tm/terminator, the opaline synthase terminator and the pea rbcS E9 terminator and the like.

The sense and antisense nucleotide sequences (segments) in the (genetically modified) P0 viral sequence according to the invention, preferably are under the control of one single promoter, especially when both segments are comprised in one single nucleotide (hairpin) sequence. They may, however, also be each under the control of a different promoter (for instance when the RNA construct is made of segments being 2 different molecules). Id est, the sense DNA sequence may be operably linked to a first promoter and the antisense DNA sequence operably linked to a second promoter. The first promoter and the second promoter may be the same promoter or may be different promoters. The promoter may be a divergent or bidirectional promoter capable of initiating transcription of DNA sequences (into the two RNA segments) on each side of the promoter.

The RNA or DNA construct or sequence according to the invention, apart from a sense and antisense modified (P0) viral nucleotide (fragment) sequence, advantageously further comprise a linker or spacer nucleotide sequence between the DNA sequences encoding the sense and antisense RNA segments It is expected that there are no length limits or sequence requirements associated with the spacer region, as long as these parameters do not interfere with the capability of the RNA regions with the sense and antisense nucleotide (segment) sequence to form a double stranded RNA. Preferably, the spacer region or sequence varies in length from about 5 to about 1000 bp, more preferably, from about 10 to about 500 bp, still more preferably from about 50 to about 200 bp.

A preferred spacer or linker nucleotide sequence is an intron sequence, preferably one in sense orientation, enhancing the efficiency of reduction of expression of the target nucleotide sequence. The enhancement in efficiency may be expressed as an increase in the frequency of plants wherein silencing occurs or as an increase in the level of reduction of viral expression.

Preferred intron nucleotide sequences (or introns) are derived from plant genes, like presumed ribosomal RNA genes or highly transcribed plant genes. These introns may be derived from any plant gene, yet preferably are derived from dicotyledonous plant genes, e.g. from *Petunia* genes, yet most preferably are derived from (sugar) beet genes. It is also possible to use only part of these (plant) introns, for instance at least the borders containing splicing signals (see below). The whole of these introns and parts thereof in the context of the invention are referred to as "intron fragments" or "intron sequences".

A preferred length for such intron nucleotide sequences is between about 5 and about 1000 bp, preferably between about 50 and about 600 bp, more preferably of between about 90 and about 550 bp. Preferred intron sequences comprise the sequence SEQ. ID. NO: 11 or 12, or even more preferably consist of the sequence SEQ. ID. NO: 11 or 12.

The RNA construct, comprising the sense and antisense nucleotide (segment) sequences capable of forming for instance a hairpin structure, which are produced by the transcription of the corresponding recombinant DNA, can also be introduced directly in a plant cell.

Such RNA molecules could be produced e. g. by
cloning the DNA region capable of being transcribed into an RNA molecule with a nucleotide sequence comprising a sense nucleotide (segment) sequence of at least 10 (preferably at least 20, 21, 22, 23, 24, 25 or more) consecutive nucleotides having between 75 and 100% sequence identity with (at least part of) the nucleotide sequence of interest and an antisense nucleotide (segment) having at least 10 nucleotides, (preferably at least about 15 nt, 20 nt, particularly at least about 50 nt, more particularly at least about 100 nt, especially at least about 150 nt, more especially at least about 200 nt, 250 nt, 300 nt, quite especially at least about 350 nt or about 400 nt,) and having between about 75% to about 100% sequence identity with the complement of nucleotides of the sense nucleotide sequence (and with the target mRNA), whereby this RNA construct (comprising a sense and an antisense segments) is capable of forming a double stranded RNA by base-pairing between the regions with sense and antisense nucleotide sequence resulting for instance in a hairpin RNA structure;

performing an in vitro transcription reaction by adding inter alia the suitable DNA-dependent RNA polymerase as well as the required reagents to generate the RNA molecules; and isolating the RNA molecules.

The invention also further provides a BMYV and/or BNYVV resistant or tolerant plant that comprises in the genome of at least part of its cells, preferably in substantially all of its cells, a (genetically modified; sense and/or antisense and/or hairpin) P0 sequence (and possibly also a sense and/or antisense and/or hairpin sequence deduced from the genome of BNYVV) according to the invention and/or a vector comprising same, which, when transcribed, yields an RNA molecule that triggers PTGS of BMYV and possibly of BNYVV. Also provided is a BMYV and/or BNYVV resistant or tolerant plant that comprise in at least part of their cells, preferably in substantially all of their cells, an RNA molecule according to the invention to achieve the above-described effect.

A "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units. The latter are also referred to as (vegetatively) reproducible structures meaning that they may be regenerated into a whole plant.

The obtained transformed plant, plant tissues and plant material can be used in a conventional breeding and plant propagation or regeneration schemes to produce more transformed plants with the same characteristics (virus resistance or tolerance) or to introduce the DNA construct according to the present invention in other varieties of the same or a related plant species.

"Virus resistance or tolerance" means herein that a resistant or tolerant cell or plant is either not susceptible or has reduced susceptibility to one or more viruses as compared to a sensitive cell or plant. In the present case, resistance and preferably extreme resistance to BMYV and/or BNYVV infections are envisaged. Tolerance, for instance, means that the usual symptoms of a virus infection are absent or reduced, or that accumulation or replication of the virus in the cell is prevented or reduced, or that movement of the virus, for instance from cell to cell is prevented or reduced.

The invention will now be further described by reference to the following detailed (non limiting) examples.

EXAMPLES

To study the functionality of the PTGS inducing P0 sequence, a binary *Agrobacterium* vector, for instance, according to FIGS. 4A and 4B was constructed.

The creation of the DNA constructs according to the invention and the cloning of these constructs into *Agrobacterium tumefaciens* ((disarmed) GV3101 strain) was performed according to methods and techniques well known in the art. The (PO) sense and antisense fragments and the introns were generated by genetic amplification (PCR) including specific restrictions sites at the ends. Mixed together with the vector backbone, only one recombinaison/insertion of the fragments was possible based on the compatibility of these specific sites at the end of the fragments.

The *Agrobacterium tumefaciens* strain GV3101 carrying a hairpin construct was used to mediate transformation of *Arabidopsis thaliana* by the Floral dip method. Leaf material of transgenic *Arabidopsis thaliana* was infected by the BMYV-2itb natural isolate using aphid transmission or by BMYV-EK strain issued from infectious clone and aphid transmitted.

For the aphid transmission experiments: to acquire the virus, aphids were allowed a 48 h acquisition access period (AAP) on purified suspension of BMYV-2itb isolate or BMYV-EK clone. After the AAP, the aphids were transferred with a fine-tipped paint brush on transgenic *Arabidopsis thaliana* leaves (10 aphids per plant) for 96 h inoculation access period (TAP). Then, the aphids were killed by insecticide treatment and the virus detection by ELISA was performed 3 weeks later on systemic leaves.

For all the experiments below, the ELISA data were evaluated by means of the SAS 9.1 software (ANOVA method) followed by the Tukey test. The P value <0.05 indicated a significant difference.

Example 1

RNA silencing mechanism targets conserved sequences and induces their degradation. The most conserved sequences within Poleroviruses reside at the 3' half of the RNA.

It is assumed that expression of the hairpin constructs having sequences deduced from conserved parts of the viral genome results (in planta) in the formation of dsRNA that is recognized and cut into duplexes of about 21-24 nts (siRNA) by the enzyme Dicer. Specific siRNAs will be loaded into a RISC complex (RNA induced silencing complex), that will on its turn target the homologous viral genomic RNA and induce degradation of the latter. As such, the virus metabolism will be severely impaired, and the symptoms of viral infection will be reduced. In the most favourable cases, total resistance will be obtained.

The inventors firstly generated two hairpins sequences derived from the viral 3'-end of the viral genome (BMYV).

The first construct harbored the CP (coat protein) sequence named hpCP and the second, the 3' end of the RT (readtrough protein) sequence with the 3' end non-coding sequence of BMYV genome called hpRT+Nc.

Both constructs were used to transform *Arabidopsis thaliana* plants and for each, ten independent transgenic lines were obtained and tested for their resistance against BMYV.

Plants expressing siRNA specific to the 3' end of viral genome were challenged with the virus. None of the transgenic plant was resistant to BMYV whatever the hpCP or hpRT+Nc hairpin used.

Example 2

Transgenic *Arabidopsis thaliana* encoding hpP0 (u) constructs according to the invention were then challenged with BMYV-2itb isolate.

Six independent transgenic *Arabidopsis thaliana* lines were created that express the hpP0 (or hpOu) mRNA. Results obtained with the construct 1 (FIG. 4A) are summarized in FIG. 5. The statistical ANOVA analysis performed revealed existing differences within ELISA values of transgenic and wild type plants (p<0.0001). Tukey test revealed the absence of significant difference between transgenic lines whereas all lines were significantly different to Co10 Inf (p<0.05) revealing the resistance of the transgenic lines toward BMYV inoculation.

P0-specific siRNA molecules were detected in the six lines but in higher levels in three resistant lines (hpP0-9, -10 and -12). No siRNA were detected in the susceptible plants (Col 0).

These results point out that hpP0 (u) constructs are suitable to induce PTGS in *Arabidopsis thaliana* plants and can induce BMYV resistance.

Example 3

The experiments from example 2 were repeated with the construct 2 (FIG. 4B) and with a higher number (eight) of transgenic *Arabidopsis thaliana* lines challenged with BMYV-2itb isolate.

The results are summarized in FIG. 6. For this construct, excepted line hpP0beet-3, all lines were resistant to BMYV as confirmed by ANOVA and Tukey statistical analysis (p<0.05). No significant difference was observed between hpP0-12 and resistant hpP0beet lines.

P0-specific siRNA molecules levels were found to be significantly higher in the resistant lines (hpP0beet-1, -2, -5, -7 and -8) than in the other lines.

Example 4

The results described in example 2 and in example 3 were repeated with both type of transgenic *Arabidopsis thaliana* lines (hpP0-9, -10, -12, hpP0beet-2, -7 and -8) and two sources of inoculum (BMYV-EK or BMYV-2itb).

The results are represented in FIG. 7. All the transgenic *Arabidopsis thaliana* lines were found resistant to BMYV-EK inoculum (p<0.05). Transgenic lines respond differently toward BMYV-2itb isolate.

Taken together, these results indicate a better protection against BMYV when transgene contains the beet intron.

Induction of PTGS by the means of a hairpin construct thus seems to be a good source of resistance against a viral infection, and in particular against BMYV.

From the above examples, it appears that the pathogen-derived hpP0 (u) resistance according to the invention is highly efficient.

The hpP0 constructs of the invention successfully induced pathogen-derived plant resistance. The tested hpP0 constructs all induced a degradation of genomic RNA via PTGS, which resulted in BMYV resistant plants.

Example 5

The inventors have tested the efficiency of other strategies using the construct hpCP comprising gene encoding the capsid protein of the BMYV genome and the 3' distal sequence (hpRT+NC construct of the BMYV gene encoding RT protein followed by the non coding extremity of the viral BMYV RNA). The inventors have discovered unexpectedly that these two additional constructs were ineffective for inducing a viral resistance into a plant.

The invention claimed is:

1. A RNA construct comprising a sense segment and an antisense segment, wherein said sense segment and said antisense segment both comprise a nucleotide fragment having at least 95% of sequence identity with at least 20 consecutive nucleotides of Beet Mild Yellowing Virus (BMYV) P0 gene or an ortholog of the BMYV P0 gene, wherein the BMYV P0 gene is as set forth in SEQ ID NO: 17, and the ortholog of the P0 gene is selected from Table 1, wherein said RNA construct decreases the expression of the said P0 gene from BMYV or of the said P0 gene ortholog.

2. The RNA construct of claim 1, wherein the sense segment and/or antisense segment(s) further comprise(s) a nucleotide fragment having at least 95% of sequence identity with the 5'-end untranslated sequence (5' UTR) adjacent to the P0 gene nucleotide sequence from the BMYV genome.

3. The RNA construct according to claim 1, wherein the sense segment and antisense segment comprise a nucleotide fragment having at least 95% of sequence identity with the P0 gene from BMYV genome.

4. The RNA construct of claim 3, wherein the sense segment and antisense segment further comprise a nucleotide fragment having at least 95% of sequence identity with P1 gene of BMYV genome.

5. The RNA construct according to the claim 1, wherein the sense segment comprises or consists of the sequence SEQ.ID.NO:1 and/or the antisense segment comprises or consists of the sequence SEQ.ID.NO:3.

6. The RNA construct according to the claim 1 wherein the sense segment and antisense segment further both comprise a nucleotide fragment having at least 95% of sequence identity with the BNYVV genome.

7. The construct according to the claim 2, wherein the fragment having at least 95% of sequence identity with the 5'-end untranslated sequence (5' UTR) adjacent to the P0 gene nucleotide comprises more than 10 nucleotides.

8. The construct according to the claim 7, wherein the fragment(s) comprise between about 15 and about 25 nucleotides.

9. A DNA construct transcriptable into the RNA construct according to the claim 1.

10. A vector comprising the nucleotide sequence of the RNA construct according to the claim 1.

11. A double stranded self-complementary RNA molecule expressed by a DNA construct transcriptable into the RNA construct, or the vector comprising the nucleotide sequence of the RNA construct, according to the claim 1.

12. A method for inducing tolerance or resistance, to at least the BMYV virus in a plant or a plant cell, the said method comprising the steps of: preparing a nucleic acid construct encoding the RNA construct according to the claim 1, and one or more regulatory sequence(s) active in the plant or the plant cell operably linked to the RNA construct, and transforming the plant cell with the nucleic acid construct, thereby inducing resistance to at least the BMYV virus in the plant or in the plant cell.

13. The method according to the claim 12, inducing tolerance or resistance to at least the BMYV virus and another virus selected from the group consisting of the Turnip yellows virus, Curcubit aphid-borne yellows virus, Potato leafroll virus, Sugarcane yellow leaf virus, Pea Enation Mosaic Virus, Beet western yellows virus-USA, Beet chlorosis virus, Cereal yellow dwarf virus and BNYVV virus.

14. A transgenic plant or a transgenic plant cell tolerant or resistant, to at least the BMYV virus and comprising the nucleic acid construct according to the claim 12.

15. The transgenic plant or transgenic plant cell of claim 14 selected from the group consisting of lettuce, cucumber, potato, sugarcane, pea, barley and sugar beet.

16. A transgenic plant tissue and/or reproducible structure derived from the transgenic plant cell of claim 15, wherein said tissue is selected from the group consisting of fruit, stem, root, tuber, and seed or wherein said reproducible structure is selected from the group consisting of calluses, buds or embryos.

17. The RNA construct according to claim 6, wherein the sense segment comprises at least 20 consecutive nucleotides of SEQ. ID.NO:5 and the antisense segment comprises at least 20 consecutive nucleotides of SEQ. IDNO: 6.

* * * * *

SEQUENCE LISTING

<160> NUMBER OF SEQ ID NOS: 18

<210> SEQ ID NO 1
<211> LENGTH: 659
<212> TYPE: DNA
<213> ORGANISM: Beet mild yellowing virus
<220> FEATURE:
<221> NAME/KEY: gene
<222> LOCATION: (1)..(659)
<223> OTHER INFORMATION: BMYV 5'UTR & P0
<220> FEATURE:
<221> NAME/KEY: 5'UTR
<222> LOCATION: (1)..(30)
<220> FEATURE:
<221> NAME/KEY: CDS
<222> LOCATION: (31)..(657)

<400> SEQUENCE: 1

```
caaaagaaac cagcgaggat ctagcagtct atg caa ttt cag ctt aaa aca aac        54
                                  Met Gln Phe Gln Leu Lys Thr Asn
                                   1               5 agt ttc act tgt tcg ttg aac cga ccg cta aca gct aca gag cga gtt         102
Ser Phe Thr Cys Ser Leu Asn Arg Pro Leu Thr Ala Thr Glu Arg Val
 10              15                  20 tta aac acc gcg tat ttt ctt acg aat cat tta ccg ctc gta act ttt        150
Leu Asn Thr Ala Tyr Phe Leu Thr Asn His Leu Pro Leu Val Thr Phe
25              30                  35                  40 gag aat gaa aac tgt att cgt tct ctt ctc gct gct ctg cct ttg ctg        198
Glu Asn Glu Asn Cys Ile Arg Ser Leu Leu Ala Ala Leu Pro Leu Leu
                 45                  50                  55 ctc agt aag cag ctc gac ccc ggg agc ttt att tac gct ccc ggg aaa        246
Leu Ser Lys Gln Leu Asp Pro Gly Ser Phe Ile Tyr Ala Pro Gly Lys
         60                  65                  70 cgc cag tct tta cga ctg gcc agg ttc tac aat tac tgc gga gcc gtg        294
Arg Gln Ser Leu Arg Leu Ala Arg Phe Tyr Asn Tyr Cys Gly Ala Val
     75                  80                  85 tta ccc agc act cgc aac att gac tta cga gtg ccc ccc aga aaa gac        342
Leu Pro Ser Thr Arg Asn Ile Asp Leu Arg Val Pro Pro Arg Lys Asp
 90                  95                 100 gtt aaa aga ttt tac ctt gcc cga aat tca ggc aga gat ctg ggg gag        390
Val Lys Arg Phe Tyr Leu Ala Arg Asn Ser Gly Arg Asp Leu Gly Glu
105                 110                 115                 120 agg cta caa cgc cgc aga gaa att ttc tct cgc ggt gaa gca gag ttt        438
Arg Leu Gln Arg Arg Arg Glu Ile Phe Ser Arg Gly Glu Ala Glu Phe
                125                 130                 135 aaa aag ttc ctt tca gta tgg tgt gct gaa agc gag aga aag cta cgg        486
Lys Lys Phe Leu Ser Val Trp Cys Ala Glu Ser Glu Arg Lys Leu Arg
            140                 145                 150 gag agt cct aaa atc gat att aga atg gac cat att att atg gtc tta        534
Glu Ser Pro Lys Ile Asp Ile Arg Met Asp His Ile Ile Met Val Leu
        155                 160                 165 cgc gat atg ggc act ctc ttg cac cgt ctg gta ctt gtt gaa gaa cta        582
Arg Asp Met Gly Thr Leu Leu His Arg Leu Val Leu Val Glu Glu Leu
    170                 175                 180 tac cat aga aat act tat gct gag ctc gct ttt tgc gtt cac cac ctt        630
Tyr His Arg Asn Thr Tyr Ala Glu Leu Ala Phe Cys Val His His Leu
185                 190                 195                 200 ttt ggt gaa gct cgt ggt atg gat ttt tg                                  659
Phe Gly Glu Ala Arg Gly Met Asp Phe
                205
```

<210> SEQ ID NO 2
<211> LENGTH: 209

<212> TYPE: PRT
<213> ORGANISM: Beet mild yellowing virus

<400> SEQUENCE: 2

```
Met Gln Phe Gln Leu Lys Thr Asn Ser Phe Thr Cys Ser Leu Asn Arg
1               5                   10                  15

Pro Leu Thr Ala Thr Glu Arg Val Leu Asn Thr Ala Tyr Phe Leu Thr
            20                  25                  30

Asn His Leu Pro Leu Val Thr Phe Glu Asn Glu Asn Cys Ile Arg Ser
        35                  40                  45

Leu Leu Ala Ala Leu Pro Leu Leu Ser Lys Gln Leu Asp Pro Gly
    50                  55                  60

Ser Phe Ile Tyr Ala Pro Gly Lys Arg Gln Ser Leu Arg Leu Ala Arg
65                  70                  75                  80

Phe Tyr Asn Tyr Cys Gly Ala Val Leu Pro Ser Thr Arg Asn Ile Asp
                85                  90                  95

Leu Arg Val Pro Pro Arg Lys Asp Val Lys Arg Phe Tyr Leu Ala Arg
            100                 105                 110

Asn Ser Gly Arg Asp Leu Gly Glu Arg Leu Gln Arg Arg Glu Ile
        115                 120                 125

Phe Ser Arg Gly Glu Ala Glu Phe Lys Lys Phe Leu Ser Val Trp Cys
    130                 135                 140

Ala Glu Ser Glu Arg Lys Leu Arg Glu Ser Pro Lys Ile Asp Ile Arg
145                 150                 155                 160

Met Asp His Ile Ile Met Val Leu Arg Asp Met Gly Thr Leu Leu His
                165                 170                 175

Arg Leu Val Leu Val Glu Glu Leu Tyr His Arg Asn Thr Tyr Ala Glu
            180                 185                 190

Leu Ala Phe Cys Val His His Leu Phe Gly Glu Ala Arg Gly Met Asp
        195                 200                 205

Phe
```

<210> SEQ ID NO 3
<211> LENGTH: 659
<212> TYPE: DNA
<213> ORGANISM: Beet mild yellowing virus
<220> FEATURE:
<221> NAME/KEY: misc_feature
<222> LOCATION: (1)..(659)
<223> OTHER INFORMATION: Antisense P0&5'UTR

<400> SEQUENCE: 3

```
caaaaatcca taccacgagc ttcaccaaaa aggtggtgaa cgcaaaaagc gagctcagca      60
taagtatttc tatggtatag ttcttcaaca agtaccagac ggtgcaagag agtgcccata    120
tcgcgtaaga ccataataat atggtccatt ctaatatcga ttttaggact ctcccgtagc    180
tttctctcgc tttcagcaca ccatactgaa aggaactttt taaactctgc ttcaccgcga    240
gagaaaattt ctctgcggcg ttgtagcctc tcccccagat ctctgcctga atttcgggca    300
aggtaaaatc ttttaacgtc ttttctgggg ggcactcgta agtcaatgtt gcgagtgctg    360
ggtaacacgg ctccgcagta attgtagaac ctggccagtc gtaaagactg gcgtttcccg    420
ggagcgtaaa taagctcccc ggggtcgagc tgcttactga gcagcaaagg cagagcagcg    480
agaagagaac gaatacagtt ttcattctca aaagttacga gcgtaaatg attcgtaaga    540 aaatacgcgt tgtttaaaac tcgctctgta gctgttagcg gtcggttcaa cgaacaagtg    600
aaactgtttg ttttaagctg aaattgcata gactgctaga tcctcgctgg tttctttg     659
```

<210> SEQ ID NO 4
<211> LENGTH: 5722
<212> TYPE: DNA
<213> ORGANISM: Beet mild yellowing virus
<220> FEATURE:
<221> NAME/KEY: misc_feature
<222> LOCATION: (1)..(5722)
<223> OTHER INFORMATION: BMYV genome

<400> SEQUENCE: 4

| | | | | | |
|---|---|---|---|---|---|
| acaaaagaaa | ccagcgagga | tctagcagtc | tatgcaattt | cagcttaaaa | caaacagttt | 60 |
| cacttgttcg | ttgaaccgac | cgctaacagc | tacagagcga | gttttaaaca | ccgcgtattt | 120 |
| tcttacgaat | catttaccgc | tcgtaacttt | tgagaatgaa | aactgtattc | gttctcttct | 180 |
| cgctgctctg | cctttgctgc | tcagtaagca | gctcgacccc | gggagcttca | tttacactcc | 240 |
| cgggaaacgc | cagtctttac | gactggccag | gttctacaat | tactgcggag | ccgtgttacc | 300 |
| cagcactcgc | aacattgact | tacgagtgcc | cccagaaaaa | gacgttaaaa | gattttacct | 360 |
| tgcccgaaat | tcaggcagag | atctggggga | gaggctacaa | cgccgcagag | aaattttctc | 420 |
| tcgcggtgaa | gcagagttta | aaagttcct | tcagtatgg | tgtgctgaaa | gcgagagaaa | 480 |
| gctacgggag | agtcctaaaa | tcgatattag | aatggaccat | attattatgg | tcttacgcga | 540 |
| tatgggcact | ctcttgcacc | gtctggtact | tgttgaagaa | ctataccata | gaaatactta | 600 |
| tgctgagctc | gcttttttgcg | ttcaccacct | ttttggtgaa | gctcgtggta | tggattttttg | 660 |
| gcggttggct | aacttccctg | gtaaatggtt | tatttgctct | cacgaaatgt | attttgaaaa | 720 |
| ctctttcatc | cagaaagagc | tacgtttgtg | agcgatctgt | aaaaggtttt | ctcacccttta | 780 |
| ccatcaaaca | aagcccgccg | cgtaattgca | ttcttcaaat | acaacacgca | gacggttccc | 840 |
| atgccggtta | tgcaacatgc | gtaaccttat | tcgacgggac | aaacggattg | ttgactgcgc | 900 |
| aacatgtagt | tgacgatttt | tacgaaggag | acccgagaaa | gactctaaaa | gtcgtctcca | 960 |
| cccgcaatgg | aaacaaaatc | ccccttgatg | aattcagagt | gacgtacaca | tctgagaaaa | 1020 |
| gggatcagtt | gttgatgcat | gggcccccaa | actgggaagg | agttcttgcc | tgcaaggcag | 1080 |
| ttcacatgat | tccggcatcg | agtgttgcaa | atcgaaagc | aactttctttt | gctctgtcgg | 1140 |
| atggtgaatg | gcattcctct | aatgccgagc | tcgttggcac | atccaagtgc | ggaaaattca | 1200 |
| tttctgtact | cagtgacaca | aagagtggtc | attcgggcac | tccctatttc | aatggtaaga | 1260 |
| gtgttcttgg | agttcacata | ggctctccga | agaatttga | gtcggaaaat | gttaactaca | 1320 |
| tgtctcctat | accacgtttt | cctggattaa | ccagcccgaa | ctacatattt | gaaaccacag | 1380 |
| cccttgctgg | aaaatttttc | agccaagagg | aagtcgaaga | gctaatggaa | gacttctctc | 1440 |
| tccaagagat | ttattctata | gcgacggcac | gtgggaagta | cataaaatat | gaggcttgtc | 1500 |
| caggtgaaga | gacattccat | gatgtgctaa | cagagtcctc | cccgatgcag | ggggaaggaa | 1560 |
| gggcggctcc | gaccgccgga | acaaccggaa | acgcaagcac | ccacgagaga | tccgcaggaa | 1620 |
| atggaaaaag | ccctcgtgct | gctccttcta | caccgcggga | acccttggtg | aaaactgcac | 1680 |
| cgcaagccac | gtacattgta | cctcaaaaga | ggaatatgac | gaatggccga | gatgctggtg | 1740 |
| ccaaattgca | ggccacgact | gccactaccg | atcaaatctc | agagataaag | aaggctctga | 1800 |
| tagacaaaat | ggatttgaaa | tcgatcgaga | gacaagtggt | agagacacta | tcgtcgatgg | 1860 |
| ccatgaagaa | gccccgctca | agagggcgga | gaagatccaa | gaacaagcaa | acaatttgg | 1920 |
| acgcttcttc | aaaacccagt | accactggga | aagagccgca | gaggtctgcc | ccggtttcat | 1980 |

```
caaagtcggt gagctcccca agttttactt ctctaaacaa aaaggatgct cggattgggg    2040
cacgaagctc accagcctcc acccagaatt ggaggagaaa acccgaggct tcgggtggcc    2100
caagttcggg ccagcggcgg aactgaaatc cttgcggcta caagccgcaa gatggctcga    2160
acgcgccgag caagttaaaa tcccttcaac tgaggaaagg gagcgcgtcg tgaggaaatg    2220
tgtggaagca ttctcgccca ctcaaacacg aggtcccatg gccacgagag gaaacaaact    2280
gtcttggaac aatttccttg aagattttaa aacggcagtt ttctctctcg agctcgaagc    2340
cggcgtaggc gtcccgtatg ttgcttacgg tcgacgcacg cacagaggct ggattgaaga    2400
tccagatctg ttgccggttt tagctcgttt caccttcgat cgattacaga agttatcgga    2460
ggtgaaattt gagcatatga gccctgaaca attggttcag gaaggtctgt gtgacccaat    2520
acggttattc gtaaaaggcg agccacacaa acaatccaaa cttgatgaag gacgctaccg    2580
cctcatcatg agtgtctcat ggttgatca actggtagcc cgggttctgt ttcaaaatca    2640
gaacaagcgc gagatcgcgc tttggagggc gattccctca aaaccggat tcggattgtc    2700 cacagacgga caagtcgtcg atttcatgca agcattatcg gcgcaggtgg gagtgaacac    2760
tgctgaatta ctccaaaatt ggaaatccca ccttattcct acagattgct ctggttttga    2820
ctggagcgtt tcggactggc ttctagagga tgaaatggaa gtccggaaca ggctcacgtt    2880
ggacataaat gatctaacca ggcgtctgcg agctggatgg cttaaatgcc tcgcaaatag    2940
tgttctctgt ctatcagatg gaacattgct ctcgcagcaa gtgcctggtg tacaaaagag    3000
tggcagctac aacacctcct cgtctaactc tagaattcga gtgatggccg cttaccactc    3060
cggagcctcc tgggccatcg ccatgggtga tgatgcccct gaatctgtag atgcagacct    3120
aagtcgatac tcatccttag gcttcaaagt cgaggtttct tcacaactgg aattctgctc    3180 tcacatttt gaggaggaga acctcgccgt tccggtaaac aaagctaaaa tgctttataa    3240
attgatacat ggttatgaac cggaatgtgg caaccttgaa gttctgacga actatcttgc    3300
agcttgtttc tcaatttaa acgagctgag atccgatcaa gaactcgttg cctccctcta    3360
tcagtggctg gtccttccag tgcagccaca aaagatataa cgagggacaa tataaacagc    3420
cgggtaaaca tcagttgcaa acgccggaag tttaaagtct gattacataa caagccaaaa    3480
tagatttcaa gttttagca ggattttcaa gtggtctatg tcagcaatac ctgtaacggt    3540
agttggcttg tatttcgtct accttaagat ttctcaccac gtcagatcaa ttgttaatga    3600
atacggtcgt gggtaggaga acgatcaatg gaagaagacg accacgtagg caaacacgac    3660
gcgctcagcg ctctcagcca gtggttgtgg tccaagcctc tcggacaaca caacgccgac    3720
ctagacgacg acgaagaggc aacaaccgga caagaagaac tgtttctacc agaggaacag    3780
gttcgagcga gacattcgtt ttctcaaaag acaatctcgc gggaagttcc agcggagcaa    3840
tcacgttcgg gccgagtcta tcagactgcc cggcattcgc tgatggaatg ctcaaggcct    3900
accatgagta taaatctca atggtcattt tggagttcgt ctccgaggcc tcttcccaaa    3960
attccggttc catcgcttac gagctggacc cacactgtaa actcagtgcc ctttcatcaa    4020
ccattaacaa gttcgggatc acaaaacccg gcaggagggc atttgcagcg tcttacatca    4080
acggggcgga ctgcatgac gttgccaagg accaattcag gatcctctac aaaggcaatg    4140
gttcttcatc gatagctggt tcttttagaa tcaccatgaa gtgccagttc cacaatccga    4200
aataggtaga caaggaaccc ggccctagcc cagggccttc tccctctcca caacccacac    4260
cctcaaagaa atatcgtttt atcgtctata ctggtgtccc tgtgacccgt ataatggccc    4320
aatccactga tgacgccatc tctctgtacg acatgccttc ccaacggttt cgctacatag    4380
```

```
aagacgagaa tatgaactgg acaaacctcg attctcgatg gtattcccag aattctttga    4440
aagccatccc aatgataata gtaccagtcc ctcaaggtga gtggactgtg gaaatttcga    4500
tggaggggta tcaaccaacc tcaagcacca cagatcctaa taaggacaaa caagatggtc    4560
ttattgcata taatgatgac ctcaaggagg gttggaatgt aggggtttat aacaatgtgg    4620
agataaccaa caataaggct gataacactt tgaagtacgg ccatccagac atggagctca    4680
atagttgtca ttttaatcaa ggacaatgtt tggaaagaga tggagatttg acttgtcacg    4740
ttaaaacaac tggtgacaat gcctccttct ttgttgttgg tcccgctgtc cagaagcaat    4800
ccaaatacaa ttatgccgtt tcatacggag cctggacaga tcggatgatg gagataggga    4860
tgatagccat agcacttgat gaacaaggct catccggttc cgcaaagata gaaagaccaa    4920
agagagtcgg gcactccatg gcagtctcaa cctgggagac tataaactta ccggagaagg    4980
aaaactccgg tgaattcaaa accgatcaaa gacaagatct caaaactcct cccacatctg    5040
gtgggagttc cgatatgccg gatatcgttc aaggaggctt accccttccc attgaagaag    5100
acattcctga tttcatcagg gatgacccct ggtccaacat accggccaag acttcgcggg    5160
aagacgaggc tgcgtcatca aagagtggtt ttaaaccccca attgaagcct cctggcttgc    5220
caaagccaca accggtcaga acgatccgaa acttcgatcc agaacctgac ttggttgagg    5280
catggcgacc tgacgtgaac cccggatatt ccaaggaaga cgtggcagcg gccactgtta    5340
tgtacggggg ttccgttaat gaaggccggt ctatgattga caagcgtgat aaagctgtgt    5400
tagacggccg caagagttgg ggttcttcct tggcgtcctc cttgacggga ggcacgctta    5460
aggcctctgc aaagtcagag aagcttgcca aactcacttc gagtgaaagg gcgcagttca    5520
aacgaattaa gcgccagcaa ggtgccacac gagcttcaga attttttagaa caacttctgg    5580 ctggcacaaa ccctgaccca aggtcctgat gaaccttttcc caatcatcac agtcaagccc    5640
gtgactttaa acgcggaacg actccgaaag gataggcaac gagtgttttta cgctgggata    5700 actccctacg gcacttcggt gt                                             5722
```

<210> SEQ ID NO 5
<211> LENGTH: 397
<212> TYPE: DNA
<213> ORGANISM: Beet necrotic yellow vein virus
<220> FEATURE:
<221> NAME/KEY: misc_feature
<222> LOCATION: (1)..(397)
<223> OTHER INFORMATION: Mutated P15 (sense)

<400> SEQUENCE: 5

```
ggtgcttgtg gttaaagtag atttatctaa tattgtattg tacatagttg ccggttgtgt     60
tgttgtcagt atgttgtact caccgttttt cagcaacgat gttaaagcgt ccagctatgc    120
gggagcaatt tttaagggga gcggctgtat catggccgcg aattcgtttg ctcaatttgg    180
gagttgcgat attccaaagc atgtagccga gtccatcact aaggttgcca ccaaagagca    240
cgatgttgac ataatggtaa aaaggggtga agtgaccgtt cgtgttgtga ctctcaccga    300
aactattttt ataatattat ctagattgtt tggtttggcg gtgttttttgt tcatgatatg    360 tttaatgtct atagtttggt tttggtatca tagataa                              397
```

<210> SEQ ID NO 6
<211> LENGTH: 397
<212> TYPE: DNA
<213> ORGANISM: Beet necrotic yellow vein virus
<220> FEATURE:

<221> NAME/KEY: misc_feature
<222> LOCATION: (1)..(397)
<223> OTHER INFORMATION: Mutated P15 BNYVV (antisense)

<400> SEQUENCE: 6
ttatctatga taccaaaacc aaactataga cattaaacat atcatgaaca aaaacaccgc 60
caaaccaaac aatctagata atattataaa aatagtttcg gtgagagtca caacacgaac 120
ggtcacttca cccctttta ccattatgtc aacatcgtgc tctttggtgg caaccttagt 180
gatggactcg gctacatgct ttggaatatc gcaactccca aattgagcaa acgaattcgc 240
ggccatgata cagccgctcc ccttaaaaat tgctcccgca tagctggacg ctttaacatc 300
gttgctgaaa aacggtgagt acaacatact gacaacaaca caaccggcaa ctatgtacaa 360
tacaatatta gataaatcta ctttaaccac aagcacc 397

<210> SEQ ID NO 7
<211> LENGTH: 1056
<212> TYPE: DNA
<213> ORGANISM: Artificial Sequence
<220> FEATURE:
<221> NAME/KEY: misc_feature
<222> LOCATION: (1)..(1056)
<223> OTHER INFORMATION: P15-P0 sense

<400> SEQUENCE: 7
ggtgcttgtg gttaaagtag atttatctaa tattgtattg tacatagttg ccggttgtgt 60
tgttgtcagt atgttgtact caccgttttt cagcaacgat gttaaagcgt ccagctatgc 120
gggagcaatt tttaagggga gcggctgtat catggccgcg aattcgtttg ctcaatttgg 180
gagttgcgat attccaaagc atgtagccga gtccatcact aaggttgcca ccaaagagca 240
cgatgttgac ataatggtaa aaaggggtga agtgaccgtt cgtgttgtga ctctcaccga 300
aactattttt ataatattat ctagattgtt tggtttggcg gtgtttttgt tcatgatatg 360
tttaatgtct atagtttggt tttggtatca tagataacaa aagaaaccag cgaggatcta 420
gcagtctatg caatttcagc ttaaaacaaa cagtttcact tgttcgttga accgaccgct 480
aacagctaca gagcgagttt taaacaccgc gtattttctt acgaatcatt taccgctcgt 540
aacttttgag aatgaaaact gtattcgttc tcttctcgct gctctgcctt tgctgctcag 600
taagcagctc gaccccggga gctttattta cgctcccggg aaacgccagt ctttacgact 660
ggccaggttc tacaattact gcggagccgt gttacccagc actcgcaaca ttgacttacg 720
agtgcccccc agaaaagacg ttaaaagatt ttaccttgcc cgaaattcag gcagagatct 780
gggggagagg ctacaacgcc gcagagaaat ttctctcgc ggtgaagcag agtttaaaaa 840
gttcctttca gtatggtgtg ctgaaagcga gagaaagcta cgggagagtc ctaaaatcga 900
tattagaatg gaccatatta ttatggtctt acgcgatatg ggcactctct tgcaccgtct 960
ggtacttgtt gaagaactat accatagaaa tacttatgct gagctcgctt tttgcgttca 1020
ccaccttttt ggtgaagctc gtggtatgga tttttg 1056

<210> SEQ ID NO 8
<211> LENGTH: 1056
<212> TYPE: DNA
<213> ORGANISM: Artificial Sequence
<220> FEATURE:
<221> NAME/KEY: misc_feature
<222> LOCATION: (1)..(1056)
<223> OTHER INFORMATION: P15 P0 antisense

<400> SEQUENCE: 8

```
caaaaatcca taccacgagc ttcaccaaaa aggtggtgaa cgcaaaaagc gagctcagca      60
taagtatttc tatggtatag ttcttcaaca agtaccagac ggtgcaagag agtgcccata     120
tcgcgtaaga ccataataat atggtccatt ctaatatcga ttttaggact ctcccgtagc     180
tttctctcgc tttcagcaca ccatactgaa aggaactttt taaactctgc ttcaccgcga     240
gagaaatttt ctctgcggcg ttgtagcctc tcccccagat ctctgcctga atttcgggca     300
aggtaaaatc ttttaacgtc ttttctgggg ggcactcgta agtcaatgtt gcgagtgctg     360
ggtaacacgg ctccgcagta attgtagaac ctggccagtc gtaaagactg gcgtttccg      420 ggagcgtaaa taaagctccc ggggtcgagc tgcttactga gcagcaaagg cagagcagcg     480
agaagagaac gaatacagtt ttcattctca aaagttacga gcggtaaatg attcgtaaga     540
aaatacgcgt gtttaaaac tcgctctgta gctgttagcg gtcggttcaa cgaacaagtg     600
aaactgtttg ttttaagctg aaattgcata gactgctaga tcctcgctgg tttcttttgt     660
tatctatgat accaaaacca aactatagac attaaacata tcatgaacaa aaacaccgcc     720
aaaccaaaca atctagataa tattataaaa atagtttcgg tgagagtcac aacacgaacg     780
gtcacttcac ccctttttac cattatgtca acatcgtgct ctttggtggc aaccttagtg     840
atggactcgg ctacatgctt tggaatatcg caactcccaa attgagcaaa cgaattcgcg     900
gccatgatac agccgctccc cttaaaaatt gctcccgcat agctgacgc tttaacatcg      960 ttgctgaaaa acggtgagta caacatactg acaacaacac aaccggcaac tatgtacaat    1020
acaatattag ataaatctac tttaaccaca agcacc                              1056

<210> SEQ ID NO 9
<211> LENGTH: 1058
<212> TYPE: DNA
<213> ORGANISM: Artificial Sequence
<220> FEATURE:
<221> NAME/KEY: misc_feature
<223> OTHER INFORMATION: P0 P15 sense

<400> SEQUENCE: 9
caaaagaaac cagcgaggat ctagcagtct atgcaatttc agcttaaaac aaacagtttc      60
acttgttcgt tgaaccgacc gctaacagct acagagcgag ttttaaacac cgcgtatttt    120
cttacgaatc atttaccgct cgtaactttt gagaatgaaa actgtattcg ttctcttctc    180
gctgctctgc ctttgctgct cagtaagcag ctcgaccccg ggagctttat ttacgctccc    240
gggaaacgcc agtctttacg actggccagg ttctacaatt actgcggagc cgtgttaccc    300
agcactcgca acattgactt acgagtgccc cccagaaaag acgttaaaag atttaccttt    360
gcccgaaatt caggcagaga tctggggag aggctacaac gccgcagaga aattttctct     420
cgcggtgaag cagagtttaa aaagttcctt tcagtatggt gtgctgaaag cgagagaaag    480
ctacgggaga gtcctaaaat cgatattaga atggaccata ttattatggt cttacgcgat    540
atgggcactc tcttgcaccg tctggtactt gttgaagaac tataccatag aaatacttat    600
gctgagctcg ctttttgcgt tcaccacctt tttggtgaag ctcgtggtat ggatttttga    660
tggtgcttgt ggttaaagta gatttatcta atattgtatt gtacatagtt gccggttgtg    720
ttgttgtcag tatgttgtac tcaccgtttt tcagcaacga tgttaaagcg tccagctatg    780
cgggagcaat ttttaagggg agcggctgta tcatggccgc gaattcgttt gctcaatttg    840
ggagttgcga tattccaaag catgtagccg agtccatcac taaggttgcc accaaagagc    900
acgatgttga cataatggta aaaggggtg aagtgaccgt tcgtgttgtg actctcaccg     960
```

```
aaactatttt tataatatta tctagattgt ttggtttggc ggtgttttg ttcatgatat    1020 gtttaatgtc tatagtttgg ttttggtatc atagataa                           1058

<210> SEQ ID NO 10
<211> LENGTH: 1572
<212> TYPE: DNA
<213> ORGANISM: Artificial Sequence
<220> FEATURE:
<221> NAME/KEY: misc_feature
<222> LOCATION: (1)..(1572)
<223> OTHER INFORMATION: P0 P15 antisense

<400> SEQUENCE: 10
ggtgcttgtg gttaaagtag atttatctaa tattgtattg tacatagttg ccggttgtgt     60
tgttgtcagt atgttgtact caccgttttt cagcaacgat gttaaagcgt ccagctatgc    120
gggagcaatt tttaagggga gcggctgtat catggccgcg aattcgtttg ctcaatttgg    180
gagttgcgat attccaaagc atgtagccga gtccatcact aaggttgcca ccaaagagca    240
cgatgttgac ataatggtaa aaagggggtga agtgaccgtt cgtgttgtga ctctcaccga   300
aactattttt ataatattat ctagattgtt tggtttggcg gtgttttgt tcatgatatg     360 tttaatgtct atagtttggt tttggtatca tagataacct aggaaattta aattaaatcc    420
tggttttata tgtactactg ttgtagctga aatttaggtc ttcttgctga atttatttct    480
gtttcgtttt cactgttatt caggggatcc taggttatct atgataccaa aaccaaacta    540
tagacattaa acatatcatg aacaaaaaca ccgccaaacc aaacaatcta gataatatta    600
taaaaatagt ttcggtgaga gtcacaacac gaacggtcac ttcaccctt tttaccatta     660 tgtcaacatc gtgctctttg gtggcaacct tagtgatgga ctcggctaca tgctttggaa    720
tatcgcaact cccaaattga gcaaacgaat tcgcggccat gatacagccg ctccccttaa    780
aaattgctcc cgcatagctg gacgctttaa catcgttgct gaaaaacggt gagtacaaca    840
tactgacaac aacacaaccg gcaactatgt acaatacaat attagataaa tctactttaa    900
ccacaagcac catcaaaaat ccataccacg agcttcacca aaaggtggt gaacgcaaaa     960 agcgagctca gcataagtat ttctatggta tagttcttca acaagtacca gacggtgcaa   1020
gagagtgccc atatcgcgta agaccataat aatatggtcc attctaatat cgattttagg   1080
actctcccgt agctttctct cgctttcagc acaccatact gaaaggaact ttttaaactc   1140
tgcttcaccg cgagagaaaa tttctctgcg gcgttgtagc ctctccccca gatctctgcc   1200
tgaatttcgg gcaaggtaaa atcttttaac gtcttttctg gggggcactc gtaagtcaat   1260
gttgcgagtg ctgggtaaca cggctccgca gtaattgtag aacctggcca gtcgtaaaga   1320
ctggcgtttc ccgggagcgt aaataaagct cccggggtcg agctgcttac tgagcagcaa   1380
aggcagagca gcgagaagag aacgaataca gttttcattc tcaaaagtta cgagcggtaa   1440
atgattcgta agaaaatacg cggtgtttaa aactcgctct gtagctgtta gcggtcggtt   1500
caacgaacaa gtgaaactgt tgttttaag ctgaaattgc atagactgct agatcctcgc    1560 tggtttctttt tg                                                       1572

<210> SEQ ID NO 11
<211> LENGTH: 1351
<212> TYPE: DNA
<213> ORGANISM: Petunia sp.
<220> FEATURE:
<221> NAME/KEY: misc_feature
<222> LOCATION: (1)..(1351)
```

<223> OTHER INFORMATION: Petunia intron

<400> SEQUENCE: 11

| gtgtaagaat | ttcttatgtt | acattattac | attcaacgtt | ttatcttaat | tggctcttca | 60 |
| tttgattgaa | atttgacaat | tatttcttgt | tttttttttt | gtcacactct | ttttgggttg | 120 |
| gggtggccga | cgaattgtgg | gaaggtagaa | agagggagg  | acttttgtta | tactccatta | 180 |
| gtaattactg | tttccgtttc | aatttatgtg | acaatatttc | cttttagtc  | ggttccaaaa | 240 |
| gaaaatgtca | gcattataaa | caatttaatt | ttgaaattac | aattttgcca | ttaataaaat | 300 |
| gatttacaac | cacaaaagta | tctatgagcc | tgtttgggtg | gcttataag  | cagcttattt | 360 |
| taagtggctt | ataagtcaaa | aagtgacant | ttttgagaag | ttagaaaatc | ctaacttctc | 420 |
| aaaaagtagc | ttttaagcca | cttatgactt | ataagtccaa | aaattttta  | gttaccaaac | 480 |
| atatattaat | gggtttataa | gcttataagc | cacttttaag | ctcacccaaa | cgggttctat | 540 |
| gtctcacttt | agactacaaa | ttttaaagt  | cttcatttat | ttcttaatct | ccgtggcgag | 600 |
| tnaaactata | acacataaag | tgaaacggag | ggaataagat | ggagtcataa | actaatccaa | 660 |
| atctatactc | tctccgttaa | tttgttttt  | agtttgattt | ggtacattaa | taaaacagat | 720 |
| ttttcgaagg | ttataaacac | agacagatgt | ttcccagcga | gctagcaaaa | ttccaagatt | 780 |
| tctgtcgaaa | attcgtgtgt | ttctagctag | tacttgatgt | tatctttaac | cttttagtaa | 840 |
| ttttttgtcc | ttttctttct | attttcatc  | ttacaatgaa | ttatgagcaa | gttccttaag | 900 |
| tagcatcaca | cgtgagatgt | tttttatgat | attgactaaa | tccatctttt | accattcctt | 960 |
| aactagtaaa | atacaacaca | tgttaattga | tacattgctt | aacactgagg | ttagaaaatt | 1020 |
| ttagaaatta | gttgtccaaa | tgctttgaaa | ttagaaatct | ttaatccctt | atttttttt  | 1080 |
| aaaatgtttt | ttctcactcc | aaagaaagag | aaactgacat | gaaagctcaa | aagatcatga | 1140 |
| atcttactaa | ctttgtggaa | ctaaatgtac | atcagaatgt | ttctgacatg | tgaaaatgaa | 1200 |
| agctcttaat | tttcttcttt | tatttattga | gggttttgc  | atgctatgca | ttcaatttga | 1260 |
| gtactttaaa | gcacctataa | acacttactt | acacttgcct | tggagtttat | gttttagtgt | 1320 |
| tttcttcaca | tcttttttgg | tcaatttgca | g          |            |            | 1351 |

<210> SEQ ID NO 12
<211> LENGTH: 91
<212> TYPE: DNA
<213> ORGANISM: Beta vulgaris
<220> FEATURE:
<221> NAME/KEY: misc_feature
<222> LOCATION: (1)..(91)
<223> OTHER INFORMATION: Beet intron

<400> SEQUENCE: 12

| taaatcctgg | ttttatatgt | actactgttg | tagctgaaat | ttaggtcttc | ttgctgaatt | 60 |
| tatttctgtt | tcgttttcac | tgttattcag | g          |            |            | 91 |

<210> SEQ ID NO 13
<211> LENGTH: 2701
<212> TYPE: DNA
<213> ORGANISM: Artificial sequence
<220> FEATURE:
<223> OTHER INFORMATION: hairpin P0
<220> FEATURE:
<221> NAME/KEY: misc_feature
<222> LOCATION: (1064)..(1064)
<223> OTHER INFORMATION: n is a, c, g, or t
<220> FEATURE:
<221> NAME/KEY: misc_feature
<222> LOCATION: (1277)..(1277)
<223> OTHER INFORMATION: n is a, c, g, or t

<400> SEQUENCE: 13

```
caaaagaaac cagcgaggat ctagcagtct atgcaatttc agcttaaaac aaacagtttc      60
acttgttcgt tgaaccgacc gctaacagct acagagcgag ttttaaacac cgcgtatttt     120
cttacgaatc atttaccgct cgtaactttt gagaatgaaa actgtattcg ttctcttctc     180
gctgctctgc ctttgctgct cagtaagcag ctcgaccccg ggagctttat ttacgctccc     240
gggaaacgcc agtctttacg actggccagg ttctacaatt actgcggagc cgtgttaccc     300
agcactcgca acattgactt acgagtgccc cccagaaaag acgttaaaag attttaccttt    360
gcccgaaatt caggcagaga tctggggggag aggctacaac gccgcagaga aattttctct    420
cgcggtgaag cagagtttaa aaagttcctt tcagtatggt gtgctgaaag cgagagaaag     480
ctacgggaga gtcctaaaat cgatattaga atggaccata ttattatggt cttacgcgat     540
atgggcactc tcttgcaccg tctggtactt gttgaagaac tataccatag aaatacttat     600
gctgagctcg cttttttgcgt tcaccacctt tttggtgaag ctcgtggtat ggattttttgc   660
ctaggaaatt taaatgtgta agaatttctt atgttacatt attacattca acgttttatc    720
ttaattggct cttcatttga ttgaaatttg acaattattt cttgtttttt tttttgtcac    780
actcttttttg ggttggggtg gccgacgaat tgtgggaagg tagaaagagg ggaggacttt   840
tgttatactc cattagtaat tactgtttcc gtttcaattt atgtgacaat atttccttttt   900
tagtcggttc caaaagaaaa tgtcagcatt ataaacaatt taattttgaa attacaatttt   960
tgccattaat aaaatgattt acaaccacaa aagtatctat gagcctgttt gggtgggctt    1020
ataagcagct tattttaagt ggcttataag tcaaaaagtg acantttttg agaagttaga    1080
aaatcctaac ttctcaaaaa gtagctttta agccacttat gacttataag tccaaaaatt    1140
tttaagttac caaacatata ttaatgggtt tataagctta taagccactt ttaagctcac    1200
ccaaacgggt tctatgtctc actttagact acaaatttta aaagtcttca tttatttctt    1260
aatctccgtg gcgagtnaaa ctataacaca taaagtgaaa cggagggaat aagatggagt    1320
cataaactaa tccaaatcta tactctctcc gttaatttgt ttttttagtttt gattttggtac 1380
attaataaaa cagatttttc gaaggttata aacacagaca gatgtttccc agcgagctag    1440
caaaattcca agatttctgt cgaaaattcg tgtgtttcta gctagtactt gatgttatct    1500
ttaacctttt agtaattttt tgtccttttc tttctatttt tcatcttaca atgaattatg    1560
agcaagttcc ttaagtagca tcacacgtga gatgttttttt atgatattga ctaaatccaa   1620
tctttaccat tccttaacta gtaaaataca acacatgtta attgatacat tgcttaacac    1680
tgaggttaga aaatttttaga aattagttgt ccaaatgctt tgaaattaga aatctttaat   1740
cccttatttt ttttttaaaat gttttttctc actccaaaga aagagaaact gacatgaaag   1800
ctcaaaagat catgaatctt actaactttg tggaactaaa tgtacatcag aatgtttctg    1860
acatgtgaaa atgaaagctc ttaattttct tctttttattt attgagggtt tttgcatgct   1920
atgcattcaa tttgagtact ttaaagcacc tataaacact tacttacact tgccttggag    1980
tttatgttttt agtgttttct tcacatcttt tttggtcaat ttgcaggtat ttggatccta   2040
ggcaaaaatc cataccacga gcttcaccaa aaaggtggtg aacgcaaaaa gcgagctcag    2100
cataagtatt tctatggtat agttcttcaa caagtaccag acggtgcaag agagtgccca    2160
tatcgcgtaa gaccataata atatggtcca ttctaatatc gattttagga ctctcccgta    2220
```

| | |
|---|---|
| gctttctctc gctttcagca caccatactg aaaggaactt tttaaactct gcttcaccgc | 2280 |
| gagagaaaat ttctctgcgg cgttgtagcc tctcccccag atctctgcct gaatttcggg | 2340 |
| caaggtaaaa tcttttaacg tcttttctgg ggggcactcg taagtcaatg ttgcgagtgc | 2400 |
| tgggtaacac ggctccgcag taattgtaga acctggccag tcgtaaagac tggcgtttcc | 2460 |
| cgggagcgta aataaagctc ccggggtcga gctgcttact gagcagcaaa ggcagagcag | 2520 |
| cgagaagaga acgaatacag ttttcattct caaaagttac gagcggtaaa tgattcgtaa | 2580 |
| gaaaatacgc ggtgtttaaa actcgctctg tagctgttag cggtcggttc aacgaacaag | 2640 |
| tgaaactgtt tgttttaagc tgaaattgca tagactgcta gatcctcgct ggtttctttt | 2700 |
| g | 2701 |

<210> SEQ ID NO 14
<211> LENGTH: 1435
<212> TYPE: DNA
<213> ORGANISM: Artificial sequence
<220> FEATURE:
<223> OTHER INFORMATION: Hairpin P0 (beet intron)
<220> FEATURE:
<221> NAME/KEY: misc_feature
<222> LOCATION: (1)..(1435)
<223> OTHER INFORMATION: Hairpin P0 (beet intron)

<400> SEQUENCE: 14

| | |
|---|---|
| caaaagaaac cagcgaggat ctagcagtct atgcaatttc agcttaaaac aaacagtttc | 60 |
| acttgttcgt tgaaccgacc gctaacagct acagagcgag ttttaaacac cgcgtatttt | 120 |
| cttacgaatc atttaccgct cgtaactttt gagaatgaaa actgtattcg ttctcttctc | 180 |
| gctgctctgc ctttgctgct cagtaagcag ctcgaccccg ggagctttat ttacgctccc | 240 |
| gggaaacgcc agtctttacg actggccagg ttctacaatt actgcggagc cgtgttaccc | 300 |
| agcactcgca acattgactt acgagtgccc cccagaaaag acgttaaaag attttacctt | 360 |
| gcccgaaatt caggcagaga tctggggggag aggctacaac gccgcagaga aattttctct | 420 |
| cgcggtgaag cagagtttaa aaagttcctt tcagtatggt gtgctgaaag cgagagaaag | 480 |
| ctacgggaga gtcctaaaat cgatattaga atggaccata ttattatggt cttacgcgat | 540 |
| atgggcactc tcttgcaccg tctggtactt gttgaagaac tataccatag aaatacttat | 600 |
| gctgagctcg ctttttgcgt tcaccacctt ttggtgaag ctcgtggtat ggattttgc | 660 |
| ctaggaaatt taaattaaat cctggtttta tatgtactac tgttgtagct gaaatttagg | 720 |
| tcttcttgct gaatttattt ctgtttcgtt ttcactgtta ttcaggggat cctaggcaaa | 780 |
| aatccatacc acgagcttca ccaaaaaggt ggtgaacgca aaaagcgagc tcagcataag | 840 |
| tatttctatg gtatagttct tcaacaagta ccagacggtg caagagagtg cccatatcgc | 900 |
| gtaagaccat aataatatgg tccattctaa tatcgatttt aggactctcc cgtagctttc | 960 |
| tctcgctttc agcacaccat actgaaagga acttttttaaa ctctgcttca ccgcgagaga | 1020 |
| aaatttctct gcggcgttgt agcctctccc ccagatctct gcctgaattt cgggcaaggt | 1080 |
| aaaatctttt aacgtctttt ctgggggggca ctcgtaagtc aatgttgcga gtgctgggta | 1140 |
| acacggctcc gcagtaattg tagaacctgg ccagtcgtaa agactggcgt ttcccggggag | 1200 |
| cgtaaataaa gctcccgggg tcgagctgct tactgagcag caaaggcaga gcagcgagaa | 1260 |
| gagaacgaat acagttttca ttctcaaaag ttacgagcgg taaatgattc gtaagaaaat | 1320 |
| acgcggtgtt taaactcgc tctgtagctg ttagcggtcg gttcaacgaa caagtgaaac | 1380 |
| tgtttgtttt aagctgaaat tgcatagact gctagatcct cgctggtttc ttttg | 1435 |

<210> SEQ ID NO 15
<211> LENGTH: 2229
<212> TYPE: DNA
<213> ORGANISM: Artificial sequence
<220> FEATURE:
<223> OTHER INFORMATION: Hairpin P15 P0

<400> SEQUENCE: 15

| | | | | | |
|---|---|---|---|---|---|
| ggtgcttgtg | gttaaagtag | atttatctaa | tattgtattg | tacatagttg | ccggttgtgt | 60 |
| tgttgtcagt | atgttgtact | caccgttttt | cagcaacgat | gttaaagcgt | ccagctatgc | 120 |
| gggagcaatt | tttaagggga | gcggctgtat | catggccgcg | aattcgtttg | ctcaatttgg | 180 |
| gagttgcgat | attccaaagc | atgtagccga | gtccatcact | aaggttgcca | ccaaagagca | 240 |
| cgatgttgac | ataatggtaa | aaaggggtga | agtgaccgtt | cgtgttgtga | ctctcaccga | 300 |
| aactattttt | ataatattat | ctagattgtt | tggtttggcg | gtgttttttgt | tcatgatatg | 360 |
| tttaatgtct | atagtttggt | tttggtatca | tagataacaa | aagaaaccag | cgaggatcta | 420 |
| gcagtctatg | caatttcagc | ttaaaacaaa | cagtttcact | tgttcgttga | accgaccgct | 480 |
| aacagctaca | gagcgagttt | taaacaccgc | gtattttctt | acgaatcatt | taccgctcgt | 540 |
| aacttttgag | aatgaaaact | gtattcgttc | tcttctcgct | gctctgcctt | tgctgctcag | 600 |
| taagcagctc | gaccccggga | gctttattta | cgctcccggg | aaacgccagt | ctttacgact | 660 |
| ggccaggttc | tacaattact | gcggagccgt | gttacccagc | actcgcaaca | ttgacttacg | 720 |
| agtgcccccc | agaaaagacg | ttaaaagatt | ttaccttgcc | cgaaattcag | gcagagatct | 780 |
| gggggagagg | ctacaacgcc | gcagagaaat | tttctctcgc | ggtgaagcag | agtttaaaaa | 840 |
| gttcctttca | gtatggtgtg | ctgaaagcga | gagaaagcta | cgggagagtc | ctaaaatcga | 900 |
| tattagaatg | gaccatatta | ttatggtctt | acgcgatatg | ggcactctct | tgcaccgtct | 960 |
| ggtacttgtt | gaagaactat | accatagaaa | tacttatgct | gagctcgctt | tttgcgttca | 1020 |
| ccaccttttt | ggtgaagctc | gtggtatgga | tttttgccta | ggaaatttaa | attaaatcct | 1080 |
| ggttttatat | gtactactgt | tgtagctgaa | atttaggtct | tcttgctgaa | tttatttctg | 1140 |
| tttcgttttc | actgttattc | aggggatcct | aggcaaaaat | ccataccacg | agcttcacca | 1200 |
| aaaaggtggt | gaacgcaaaa | agcgagctca | gcataagtat | ttctatggta | tagttcttca | 1260 |
| acaagtacca | gacggtgcaa | gagagtgccc | atatcgcgta | agaccataat | aatatggtcc | 1320 |
| attctaatat | cgattttagg | actctcccgt | agctttctct | cgctttcagc | acaccatact | 1380 |
| gaaaggaact | ttttaaactc | tgcttcaccg | cgagagaaaa | tttctctgcg | gcgttgtagc | 1440 |
| ctctccccca | gatctctgcc | tgaatttcgg | gcaaggtaaa | atcttttaac | gtcttttctg | 1500 |
| gggggcactc | gtaagtcaat | gttgcgagtg | ctgggtaaca | cggctccgca | gtaattgtag | 1560 |
| aacctggcca | gtcgtaaaga | ctggcgtttc | ccgggagcgt | aaataaagct | cccggggtcg | 1620 |
| agctgcttac | tgagcagcaa | aggcagagca | gcgagaagag | aacgaataca | gttttcattc | 1680 |
| tcaaaagtta | cgagcggtaa | atgattcgta | agaaaatacg | cggtgtttaa | aactcgctct | 1740 |
| gtagctgtta | gcggtcggtt | caacgaacaa | gtgaaactgt | tgttttaag | ctgaaattgc | 1800 |
| atagactgct | agatcctcgc | tggtttcttt | tgttatctat | gataccaaaa | ccaaactata | 1860 |
| gacattaaac | atatcatgaa | caaaaacacc | gccaaaccaa | acaatctaga | taatattata | 1920 |
| aaaatagttt | cggtgagagt | cacaacacga | acggtcactt | cacccctttt | taccattatg | 1980 |
| tcaacatcgt | gctctttggt | ggcaacctta | gtgatggact | cggctacatg | ctttggaata | 2040 |

```
tcgcaactcc caaattgagc aaacgaattc gcggccatga tacagccgct ccccttaaaa    2100
attgctcccg catagctgga cgcttttaaca tcgttgctga aaaacggtga gtacaacata    2160
ctgacaacaa cacaaccggc aactatgtac aatacaatat tagataaatc tactttaacc    2220
acaagcacc                                                            2229

<210> SEQ ID NO 16
<211> LENGTH: 2233
<212> TYPE: DNA
<213> ORGANISM: Artificial sequence
<220> FEATURE:
<223> OTHER INFORMATION: hairpin P0 P15

<400> SEQUENCE: 16
caaaagaaac cagcgaggat ctagcagtct atgcaatttc agcttaaaac aaacagtttc      60
acttgttcgt tgaaccgacc gctaacagct acagagcgag ttttaaacac cgcgtatttt     120
cttacgaatc atttaccgct cgtaactttt gagaatgaaa actgtattcg ttctcttctc     180
gctgctctgc ctttgctgct cagtaagcag ctcgaccccg ggagctttat ttacgctccc     240
gggaaacgcc agtctttacg actggccagg ttctacaatt actgcggagc cgtgttaccc     300
agcactcgca acattgactt acgagtgccc cccagaaaag acgttaaaag attttaccttt    360 gcccgaaatt caggcagaga tctgggggag aggctacaac gccgcagaga aattttctct     420
cgcggtgaag cagagtttaa aaagttcctt tcagtatggt gtgctgaaag cgagagaaag     480
ctacgggaga gtcctaaaat cgatattaga atggaccata ttattatggt cttacgcgat     540
atgggcactc tcttgcaccg tctggtactt gttgaagaac tataccatag aaatacttat     600
gctgagctcg cttttttgcgt tcaccacctt tttggtgaag ctcgtggtat ggattttttga   660 tggtgcttgt ggttaaagta gatttatcta atattgtatt gtacatagtt gccggttgtg     720
ttgttgtcag tatgttgtac tcaccgtttt tcagcaacga tgttaaagcg tccagctatg     780
cgggagcaat ttttaagggg agcggctgta tcatggccgc gaattcgttt gctcaatttg     840
ggagttgcga tattccaaag catgtagccg agtccatcac taaggttgcc accaaagagc     900
acgatgttga cataatggta aaagggggtg aagtgaccgt tcgtgttgtg actctcaccg     960
aaactatttt tataatatta tctagattgt ttggtttggc ggtgttttttg ttcatgatat    1020 gtttaatgtc tatagtttgg ttttggtatc atagataacc taggaaattt aaattaaatc    1080
ctggttttat atgtactact gttgtagctg aaatttaggt cttcttgctg aatttatttc    1140
tgtttcgttt tcactgttat tcaggggatc ctaggttatc tatgatacca aaaccaaact    1200
atagacatta aacatatcat gaacaaaaac accgccaaac caaacaatct agataatatt   1260
ataaaaatag tttcggtgag agtcacaaca cgaacggtca cttcaccccct ttttaccatt   1320 atgtcaacat cgtgctcttt ggtggcaacc ttagtgatgg actcggctac atgctttgga   1380
atatcgcaac tcccaaattg agcaaacgaa ttcgcggcca tgatacagcc gctccccttta  1440 aaaattgctc ccgcatagct ggacgcttta acatcgttgc tgaaaaacgg tgagtacaac    1500
atactgacaa caacacaacc ggcaactatg tacaatacaa tattagataa atctactttta  1560 accacaagca ccatcaaaaa tccataccac gagcttcacc aaaaaggtgg tgaacgcaaa   1620
aagcgagctc agcataagta tttctatggt atagttcttc aacaagtacc agacggtgca    1680
agagagtgcc catatcgcgt aagaccataa taatatggtc cattctaata tcgattttag    1740
gactctcccg tagctttctc tcgctttcag cacaccatac tgaaaggaac ttttttaaact   1800 ctgcttcacc gcgagagaaa atttctctgc ggcgttgtag cctctcccccc agatctctgc   1860
```

```
ctgaatttcg ggcaaggtaa aatcttttaa cgtctttct gggggcact cgtaagtcaa    1920 tgttgcgagt gctgggtaac acggctccgc agtaattgta gaacctggcc agtcgtaaag    1980
actggcgttt cccgggagcg taaataaagc tcccggggtc gagctgctta ctgagcagca    2040
aaggcagagc agcgagaaga gaacgaatac agttttcatt ctcaaaagtt acgagcggta    2100
aatgattcgt aagaaaatac gcggtgttta aaactcgctc tgtagctgtt agcggtcggt    2160
tcaacgaaca agtgaaactg tttgttttaa gctgaaattg catagactgc tagatcctcg    2220
ctggtttctt ttg                                                        2233

<210> SEQ ID NO 17
<211> LENGTH: 720
<212> TYPE: DNA
<213> ORGANISM: Beet mild yellowing virus
<220> FEATURE:
<221> NAME/KEY: CDS
<222> LOCATION: (1)..(720)
<223> OTHER INFORMATION: P0 protein of BMYV

<400> SEQUENCE: 17 atg caa ttt cag ctt aaa aca aac agt ttc act tgt tcg ttg aac cga      48
Met Gln Phe Gln Leu Lys Thr Asn Ser Phe Thr Cys Ser Leu Asn Arg
1               5                   10                  15 ccg cta aca gct aca gag cga gtt tta aac acc gcg tat ttt ctt acg      96
Pro Leu Thr Ala Thr Glu Arg Val Leu Asn Thr Ala Tyr Phe Leu Thr
                20                  25                  30 aat cat tta ccg ctc gta act ttt gag aat gaa aac tgt att cgt tct     144
Asn His Leu Pro Leu Val Thr Phe Glu Asn Glu Asn Cys Ile Arg Ser
            35                  40                  45 ctt ctc gct gct ctg cct ttg ctg ctc agt aag cag ctc gac ccc ggg     192
Leu Leu Ala Ala Leu Pro Leu Leu Leu Ser Lys Gln Leu Asp Pro Gly
        50                  55                  60 agc ttc att tac act ccc ggg aaa cgc cag tct tta cga ctg gcc agg     240
Ser Phe Ile Tyr Thr Pro Gly Lys Arg Gln Ser Leu Arg Leu Ala Arg
65                  70                  75                  80 ttc tac aat tac tgc gga gcc gtg tta ccc agc act cgc aac att gac     288
Phe Tyr Asn Tyr Cys Gly Ala Val Leu Pro Ser Thr Arg Asn Ile Asp
                85                  90                  95 tta cga gtg ccc ccc aga aaa gac gtt aaa aga ttt tac ctt gcc cga     336
Leu Arg Val Pro Pro Arg Lys Asp Val Lys Arg Phe Tyr Leu Ala Arg
            100                 105                 110 aat tca ggc aga gat ctg ggg gag agg cta caa cgc cgc aga gaa att     384
Asn Ser Gly Arg Asp Leu Gly Glu Arg Leu Gln Arg Arg Arg Glu Ile
        115                 120                 125 ttc tct cgc ggt gaa gca gag ttt aaa aag ttc ctt tca gta tgg tgt     432
Phe Ser Arg Gly Glu Ala Glu Phe Lys Lys Phe Leu Ser Val Trp Cys
    130                 135                 140 gct gaa agc gag aga aag cta cgg gag agt cct aaa atc gat att aga     480
Ala Glu Ser Glu Arg Lys Leu Arg Glu Ser Pro Lys Ile Asp Ile Arg
145                 150                 155                 160 atg gac cat att att atg gtc tta cgc gat atg ggc act ctc ttg cac     528
Met Asp His Ile Ile Met Val Leu Arg Asp Met Gly Thr Leu Leu His
                165                 170                 175 cgt ctg gta ctt gtt gaa gaa cta tac cat aga aat act tat gct gag     576
Arg Leu Val Leu Val Glu Glu Leu Tyr His Arg Asn Thr Tyr Ala Glu
            180                 185                 190 ctc gct ttt tgc gtt cac cac ctt ttt ggt gaa gct cgt ggt atg gat     624
Leu Ala Phe Cys Val His His Leu Phe Gly Glu Ala Arg Gly Met Asp
        195                 200                 205
```

```
ttt tgg cgg ttg gct aac ttc cct ggt aaa tgg ttt att tgc tct cac      672
Phe Trp Arg Leu Ala Asn Phe Pro Gly Lys Trp Phe Ile Cys Ser His
    210                 215                 220 gaa atg tat ttt gaa aac tct ttc atc cag aaa gag cta cgt ttg tga      720
Glu Met Tyr Phe Glu Asn Ser Phe Ile Gln Lys Glu Leu Arg Leu
225                 230                 235
```

<210> SEQ ID NO 18
<211> LENGTH: 239
<212> TYPE: PRT
<213> ORGANISM: Beet mild yellowing virus

<400> SEQUENCE: 18

```
Met Gln Phe Gln Leu Lys Thr Asn Ser Phe Thr Cys Ser Leu Asn Arg
1               5                   10                  15

Pro Leu Thr Ala Thr Glu Arg Val Leu Asn Thr Ala Tyr Phe Leu Thr
            20                  25                  30

Asn His Leu Pro Leu Val Thr Phe Glu Asn Glu Asn Cys Ile Arg Ser
        35                  40                  45

Leu Leu Ala Ala Leu Pro Leu Leu Ser Lys Gln Leu Asp Pro Gly
    50                  55                  60

Ser Phe Ile Tyr Thr Pro Gly Lys Arg Gln Ser Leu Arg Leu Ala Arg
65                  70                  75                  80

Phe Tyr Asn Tyr Cys Gly Ala Val Leu Pro Ser Thr Arg Asn Ile Asp
                85                  90                  95

Leu Arg Val Pro Pro Arg Lys Asp Val Lys Arg Phe Tyr Leu Ala Arg
                100                 105                 110

Asn Ser Gly Arg Asp Leu Gly Glu Arg Leu Gln Arg Arg Glu Ile
            115                 120                 125

Phe Ser Arg Gly Glu Ala Glu Phe Lys Lys Phe Leu Ser Val Trp Cys
            130                 135                 140

Ala Glu Ser Glu Arg Lys Leu Arg Glu Ser Pro Lys Ile Asp Ile Arg
145                 150                 155                 160

Met Asp His Ile Ile Met Val Leu Arg Asp Met Gly Thr Leu Leu His
                165                 170                 175

Arg Leu Val Leu Val Glu Glu Leu Tyr His Arg Asn Thr Tyr Ala Glu
            180                 185                 190

Leu Ala Phe Cys Val His His Leu Phe Gly Glu Ala Arg Gly Met Asp
            195                 200                 205

Phe Trp Arg Leu Ala Asn Phe Pro Gly Lys Trp Phe Ile Cys Ser His
    210                 215                 220

Glu Met Tyr Phe Glu Asn Ser Phe Ile Gln Lys Glu Leu Arg Leu
225                 230                 235
```